US011000429B2

(12) United States Patent
Uda et al.

(10) Patent No.: US 11,000,429 B2
(45) Date of Patent: May 11, 2021

(54) NONWOVEN FABRIC FOR ABSORBENT ARTICLE

(71) Applicant: UNICHARM CORPORATION, Ehime (JP)

(72) Inventors: Masashi Uda, Kagawa (JP); Shinichi Ishikawa, Kagawa (JP); Ryota Kawamori, Kagawa (JP); Takashi Maruyama, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 239 days.

(21) Appl. No.: 16/300,114

(22) PCT Filed: Jun. 1, 2016

(86) PCT No.: PCT/JP2016/066264
§ 371 (c)(1),
(2) Date: Nov. 9, 2018

(87) PCT Pub. No.: WO2017/195386
PCT Pub. Date: Nov. 16, 2017

(65) Prior Publication Data

US 2019/0142654 A1 May 16, 2019

(30) Foreign Application Priority Data

May 13, 2016 (JP) ............................ JP2016-097426

(51) Int. Cl.
*A61F 13/15* (2006.01)
*A61F 13/511* (2006.01)
(Continued)

(52) U.S. Cl.
CPC .. *A61F 13/51108* (2013.01); *A61F 13/15203* (2013.01); *A61F 13/15731* (2013.01);
(Continued)

(58) Field of Classification Search
CPC .......... A61F 13/51108; A61F 13/15203; A61F 13/5126; A61F 2013/15715; A61F 13/494;
(Continued)

(56) References Cited

U.S. PATENT DOCUMENTS

| | | | |
|---|---|---|---|
| 6,586,076 B1 | 7/2003 | Mizutani et al. |
| 2002/0058128 A1 | 5/2002 | Toyoshima et al. |

(Continued)

FOREIGN PATENT DOCUMENTS

| | | |
|---|---|---|
| CN | 1294904 A | 5/2001 |
| CN | 101790606 A | 7/2010 |

(Continued)

OTHER PUBLICATIONS

International Search Report in Application No. PCT/JP2016/066264, dated Aug. 30, 2016, 3pp.

*Primary Examiner* — Jeremy R Pierce
(74) *Attorney, Agent, or Firm* — Hauptman Ham, LLP

(57) ABSTRACT

A nonwoven fabric for an absorbent article has a plurality of first ridges and a plurality of first grooves on a first surface, each of the first ridges extending in a first direction and being provided with a first top surface including a first top section and first side surfaces, and each of the first grooves extending in the first direction; each of the first grooves of the nonwoven fabric has a plurality of second ridges and a plurality of bottom sections on the first surface, each of the second grooves being contiguous with two adjacent first ridges among the plurality of first ridges and having a second top section; the nonwoven fabric is provided with a plurality of predetermined recess units; and in each of the plurality of recess units, the fiber density of the first surface is lower than the fiber density of the first top surface.

12 Claims, 24 Drawing Sheets

(51) Int. Cl.
*A61F 13/512* (2006.01)
*A61F 13/494* (2006.01)

(52) U.S. Cl.
CPC .......... *A61F 13/494* (2013.01); *A61F 13/512* (2013.01); *A61F 13/5126* (2013.01); *A61F 2013/15422* (2013.01); *A61F 2013/15715* (2013.01); *A61F 2013/4948* (2013.01)

(58) Field of Classification Search
CPC .... A61F 2013/15422; A61F 2013/4948; A61F 13/13731
See application file for complete search history.

(56) References Cited

U.S. PATENT DOCUMENTS

| | | | |
|---|---|---|---|
| 2010/0249740 A1 | 9/2010 | Miyamoto et al. | |
| 2012/0196091 A1 | 8/2012 | Mizutani et al. | |
| 2013/0158497 A1 | 6/2013 | Yamaguchi et al. | |
| 2015/0057627 A1* | 2/2015 | Noda | A61F 13/51108 604/367 |
| 2016/0074249 A1* | 3/2016 | Rosati | A61F 13/537 604/378 |
| 2018/0140479 A1 | 5/2018 | Uda et al. | |

FOREIGN PATENT DOCUMENTS

| | | | |
|---|---|---|---|
| EP | 1090615 | A1 | 4/2001 |
| JP | 2001-95845 | A | 4/2001 |
| JP | 2002-165830 | A | 6/2002 |
| JP | 2007-167212 | A | 7/2007 |
| JP | 2009-291473 | A | 12/2009 |
| JP | 5829326 | B1 | 12/2015 |
| JP | 5829327 | B1 | 12/2015 |
| JP | 5829349 | B1 | 12/2015 |
| WO | 2009/028236 | A1 | 3/2009 |
| WO | 2011/043180 | A1 | 4/2011 |
| WO | 2012/029391 | A1 | 3/2012 |
| WO | 2013/129327 | A1 | 9/2013 |

* cited by examiner

NONWOVEN FABRIC FOR ABSORBENT ARTICLE

RELATED APPLICATIONS

The present application is a National Phase of International Application Number PCT/JP2016/066264, filed on Jun. 1, 2016, and claims priority to Japanese Application No. 2016-097426, filed on May 13, 2016.

FIELD

The present disclosure relates to a nonwoven fabric for an absorbent article.

BACKGROUND

A top sheet has been considered in which it is difficult for highly viscous excrement adhered thereto to return to the skin of the wearer, after an absorbent article absorbs the highly viscous excrement such as loose stool, highly viscous menstrual blood, etc.

For example, in Patent Document 1, a top sheet for an absorbent article is described (claim 1) in which recessed and protruded shapes are formed on the surface side being in contact with the skin at the time of being worn, characterized in that, at the time when the absorbent article in which the top sheet is used is being worn, the recessed and protruded shapes deform flexibly in accordance with the shape and the motion of the body, and the recessed portions of the recessed and protruded shapes capture the highly viscous excrement so as to let the highly viscous excrement be separated from the body.

According to the top sheet described in Patent Document 1, as described in claim 1, the recessed portions of the recessed and protruded shapes capture the highly viscous excrement so as to let the highly viscous excrement be separated from the body of the wearer.

In Patent Document 2, a nonwoven fabric for an absorbent article which includes thermoplastic resin fibers, the nonwoven fabric including a first surface, a second surface on the opposite side of the first surface, protruded portions which protrude toward the first surface side, and groove portions which are dented toward the second surface side, wherein the protruded portions are extended toward a first direction of a surface of the nonwoven fabric, and are provided in a plurality of columns with a predetermined interval in a second direction which is orthogonal to the first direction in the surface of the nonwoven fabric; the groove portions are extended in the first direction in a space between the adjacent protruded portions with respect to the second direction, and include a plurality of recessed portions provided discontinuously with respect to the first direction, at the groove bottom portions of the groove portions, each of which having a bottom portion positioned on the further second surface side than the groove bottom portions of the groove portions; and at least a part of a circumferential surface of the recessed portions includes a hole portion being connected to the second surface. Further, the nonwoven fabric which has the similar shape is also described in Patent Documents 3 and 4.

PRIOR ART DOCUMENTS

Patent Documents

[Patent Document 1] Japanese Unexamined Patent Publication No. 2002-165830

[Patent Document 2] Japanese Examined Patent Publication No. 5829326

[Patent Document 3] Japanese Examined Patent Publication No. 5829327

[Patent Document 4] Japanese Examined Patent Publication No. 5829349

DISCLOSURE OF THE INVENTION

Problems to be Solved by the Invention

However, according to the top sheet described in Patent Document 1, when the height difference of the recessed and protruded shapes is larger, the recessed and protruded shapes are crushed while being sold in a state of being housed in a package, etc., or while being worn, and it is difficult for the recessed portions of the recessed and protruded shapes to capture the highly viscous excrement. Further, when the height of the recessed and protruded shapes is made to be lower so that it is difficult for the recessed and protruded shapes to be crushed, it would be difficult to let the highly viscous excrement be separated from the body of the wearer after the recessed portions of the recessed and protruded shapes capture the highly viscous excrement.

Further, in the top sheet described in Patent Document 1, the top sheet itself only lets the highly viscous excrement be separated from the wearer, and does not actively transfer the separated highly viscous excrement to an absorption layer.

In the nonwoven fabric for an absorbent article described in Patent Documents 2 to 4, separating the highly viscous excrement from the body of the wearer after the highly viscous excrement is captured is not considered.

Accordingly, the present disclosure aims to provide a nonwoven fabric for an absorbent article which, when being used for an absorbent article, can separate the highly viscous excrement from the skin of the wearer when being worn, and can let the separated highly viscous excrement permeate from the first surface to the second surface.

Means for Solving the Problems

The inventors of the present invention has found out that a nonwoven fabric for an absorbent article, which includes a first surface and a second surface, and further includes a first direction, a second direction that is orthogonal to the first direction, and a thickness direction, wherein the nonwoven fabric includes, in the first surface, a plurality of first ridge portions each of which extending in the first direction and including a first top surface that includes a first top portion, and a first side surface; and a plurality of first groove portions each of which extending in the first direction, the each of the plurality of first ridge portions and the each of the plurality of first groove portions being disposed alternately in the second direction, the nonwoven fabric includes, in the each of the plurality of first groove portions, in the first surface, a plurality of second ridge portions each of which being connected to two adjacent first ridge portions among the plurality of first ridge portions and including a second top portion; and a plurality of bottom portions, the each of the plurality of second ridge portions and each of the plurality of bottom portions being disposed alternately in the first direction, the nonwoven fabric includes a plurality of dented units each of which including one of the plurality of bottom portions and being partitioned by virtual surfaces, each of which extending in the thickness direction, and passing through first top portions of two first ridge portions being adjacent to the one of the plurality of bottom portions, and passing through second top portions of two second ridge portions being adjacent to the one of the plurality of bottom portions, and in the each of the plurality of dented units, a fiber density of the first side surface is lower than a fiber density of the first top surface, is the solution to the problem.

Effects of the Invention

The nonwoven fabric for an absorbent article according to the present disclosure can, when being used for an absorbent article, separate the highly viscous excrement from the skin of the wearer when being worn, and can let at least a part of the separated highly viscous excrement permeate from the first surface to the second surface.

MODE FOR CARRYING OUT THE INVENTION

Definitions

Figure 1:
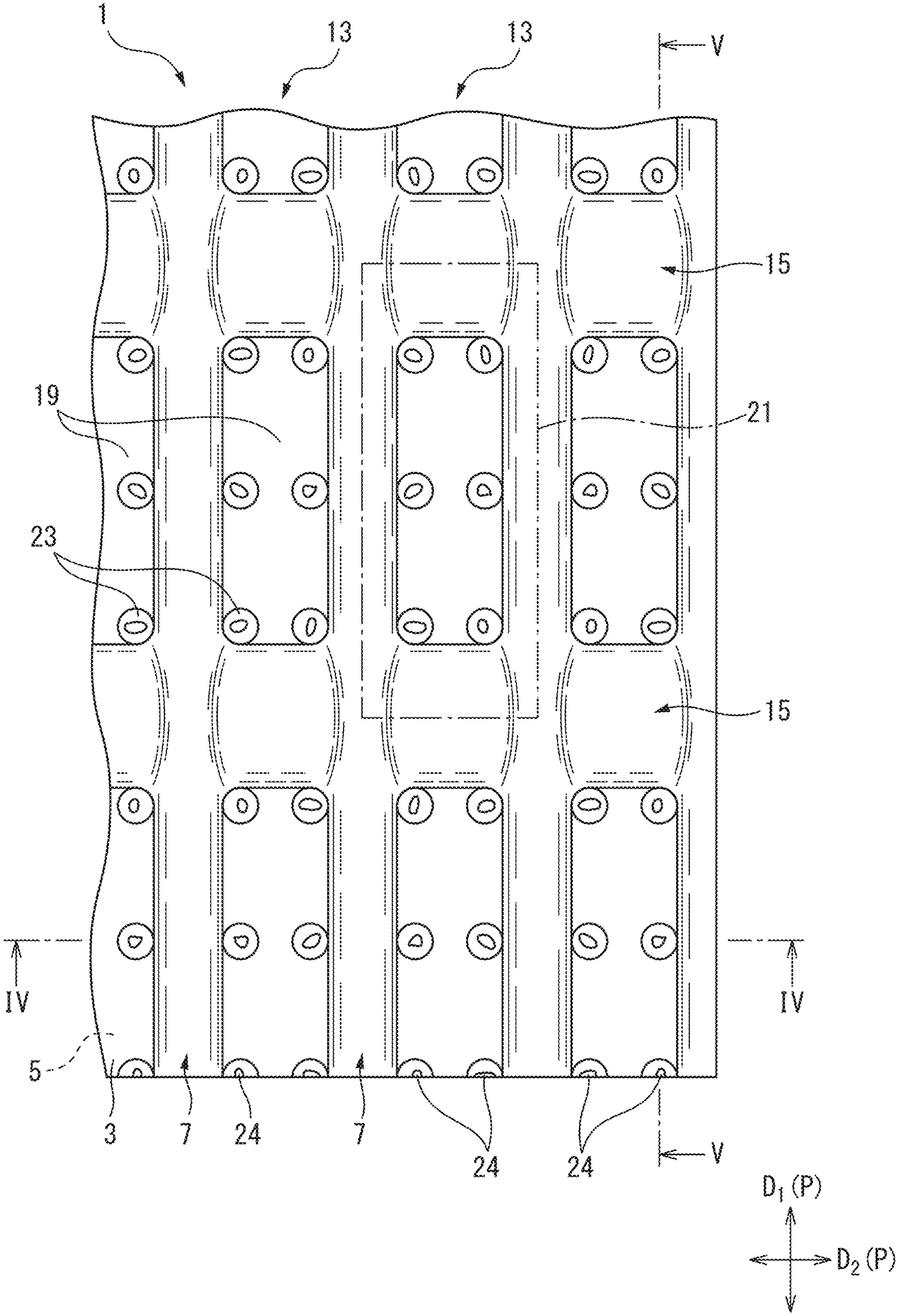
FIG. 1 is a plan view of the nonwoven fabric 1 according to the first embodiment on the first surface 3 side.

The Reference Plane of "the Ridge Portion", "the Groove Portion", "the Recessed Portion", and the "Protruded Portion", with Regard to the Nonwoven Fabric In the present description, the reference plane of "the ridge portion" (for example, the first ridge portion, the second ridge portion, and the third ridge portion), "the groove portion" (for example, the first ridge portion corresponding groove portion, the second ridge portion corresponding groove portion, and the third ridge portion corresponding groove portion), "the recessed portion", and the "protruded portion" is the bottom portion. For example, the ridge portion in the first surface is protruded in the thickness direction of the nonwoven fabric (in a direction from the second surface to the first surface), from the first surface of the bottom portion, and the recessed portion in the first surface is recessed in the thickness direction of the nonwoven fabric (in a direction from the first surface to the second surface), from the first surface of the bottom portion.

In the same manner, the groove portion in the second surface is recessed in the thickness direction of the nonwoven fabric (in a direction from the second surface to the first surface), from the second surface of the bottom portion, and the protruded portion in the second surface is protruded in the thickness direction of the nonwoven fabric (in a direction from the first surface to the second surface), from the second surface of the bottom portion.

The "Height" of the Ridge Portion of the Nonwoven Fabric

In the present description, the height of the ridge portion of the nonwoven fabric means the distance in the thickness direction of the nonwoven fabric from the first surface of the bottom portion to the first surface of the top portion of the ridge portion (for example, the first top portion, the second top portion, and the third top portion), with the first surface of the bottom portion as the reference. Incidentally, the top portion of the ridge portion is described later.

Incidentally, the height of the ridge portion is measured by using a two dimensional laser displacement meter. As the two dimensional laser displacement meter, for example, high precision two dimensional laser displacement meter LJ-G series (model: LJ-G030) manufactured by Keyence Corporation may be mentioned.

The "Pitch" of the Ridge Portion of the Nonwoven Fabric

In the present description, the "pitch" of the ridge portion of the nonwoven fabric is a term used inside the dented unit, and means the distance in a direction (for example, the second direction) orthogonal to the direction in which the ridge portion extends (for example, the first direction), from the top portion of one ridge portion to the top portion of the target ridge portion.

The "Top Portion", the "Top Surface", and the "Side Surface" of the Ridge Portion of the Nonwoven Fabric In the present description, the "top portion" of the ridge portion of the nonwoven fabric means the virtual line in which points are connected in the direction in which the ridge portion extends, the points having the highest height in the ridge portion in the direction orthogonal to the direction in which the ridge portion extends.

Further, the "top surface", and the "side surface" of the ridge portion of the nonwoven fabric are terms so as to partition the ridge portion. In the dented unit, a virtual plane which is parallel to the plane direction is assumed at the position of 70% of the height of the ridge portion, and among the ridge portion, the portion higher than such a virtual plane is referred to as the top surface, and the portion having the same height as such a virtual plane or the portion lower than the virtual plane is referred to as the side surface.

The present disclosure relates to the following aspects.

[Aspect 1]

A nonwoven fabric for an absorbent article, which includes a first surface and a second surface, and further includes a first direction, a second direction that is orthogonal to the first direction, and a thickness direction, wherein the nonwoven fabric includes, in the first surface, a plurality of first ridge portions each of which extending in the first direction and including a first top surface that includes a first top portion, and a first side surface; and a plurality of first groove portions each of which extending in the first direction, the each of the plurality of first ridge portions and the each of the plurality of first groove portions being disposed alternately in the second direction, the nonwoven fabric includes, in the each of the plurality of first groove portions, in the first surface, a plurality of second ridge portions each of which being connected to two adjacent first ridge portions among the plurality of first ridge portions and including a second top portion; and a plurality of bottom portions, the each of the plurality of second ridge portions and each of the plurality of bottom portions being disposed alternately in the first direction, the nonwoven fabric includes a plurality of dented units each of which including one of the plurality of bottom portions and being partitioned by virtual surfaces, each of which extending in the thickness direction, and passing through first top portions of two first ridge portions being adjacent to the one of the plurality of bottom portions, and passing through second top portions of two second ridge portions being adjacent to the one of the plurality of bottom portions, and in the each of the plurality of dented units, a fiber density of the first side surface is lower than a fiber density of the first top surface.

The nonwoven fabric includes a plurality of dented units, whereby in a case in which the nonwoven fabric is used for an absorbent article, and more particularly, is used as a liquid permeable sheet of an absorbent article, while housing highly viscous excrement which has reached the nonwoven fabric in the housing space of the plurality of dented units, the highly viscous excrement can be separated from the skin of the wearer.

Further, in each of the plurality of dented units, two second ridge portions have a configuration of being connected to two adjacent first ridge portions, whereby even in a case in which body pressure of the wearer, etc., is applied to the nonwoven fabric, since the second ridge portion can support the first ridge portion and the first ridge portion can support the second ridge portion, it is difficult for both the first ridge portion and the second ridge portion, as well as the housing space of the dented units, to be crushed. Still further, even if the first ridge portion and the second ridge portion are temporarily crushed by body pressure, etc., and the housing space is made to be temporarily smaller, since it is easy for the first ridge portion and the second ridge portion to return to the original shape, it is also easy for the size of the housing space to return to the original. Accordingly, the plurality of dented units can separate the highly viscous excrement which is housed in the housing space thereof from the skin of the wearer.

Still further, in each of the plurality of dented units of the nonwoven fabric, since the fiber density in the fiber density of the first ridge portion is lower than the fiber density of the first top surface, each of the plurality of dented units can let the highly viscous excrement which is housed in the housing space thereof permeate from the first surface to the second surface through the first side surface, can make the volume of the housed highly viscous excrement smaller, and can separate the highly viscous excrement which is housed in the plurality of dented units from the wearer. Still further, the plurality of dented units can make more room for housing the highly viscous excrement.

As described above, it is difficult for the nonwoven fabric to give a rash to the skin of the wearer.

[Aspect 2]

The nonwoven fabric according to aspect 1, wherein in the each of the plurality of dented units, heights of the two first ridge portions are higher than heights of the two second ridge portions.

In each of the plurality of dented units of the nonwoven fabric, since the height of the first ridge portions is higher than the height of the second ridge portions, it is difficult for the second ridge portions to be crushed due to it being difficult to receive influence of body pressure, etc., and it is also difficult for the first ridge portions which are supported by the second ridge portions to be crushed. Further, in the nonwoven fabric, in a case in which highly viscous excrement which is housed in a housing space of one dented unit is about to overflow, the nonwoven fabric can deliver the highly viscous excrement to the dented unit adjacent in the first direction beyond the second ridge portion with a low height. Accordingly, it is difficult for the highly viscous excrement to reach the first top portion of the first ridge portion with a higher height than the second top portion of the second ridge portion. Consequently, the plurality of dented units can separate the highly viscous excrement which is housed in the housing space thereof from the skin of the wearer.

[Aspect 3]

The nonwoven fabric according to aspect 1 or 2, wherein the each of the plurality of second ridge portions is partitioned by the second top surface and the second side surface, and in the each of the plurality of dented units, a fiber density of the second side surface is lower than a fiber density of the second top surface.

In each of the plurality of dented units of the nonwoven fabric, since the fiber density of the second side surface of the second ridge portion is lower than the fiber density of the second top surface, each of the plurality of dented units can let the highly viscous excrement which is housed in the housing space thereof permeate from the first surface to the second surface through the second side surface, can make the volume of the housed highly viscous excrement smaller, and can separate the highly viscous excrement which is housed in the plurality of dented units from the wearer. Still further, the plurality of dented units can make more room for housing the highly viscous excrement.

[Aspect 4]

The nonwoven fabric according to any one of aspects 1 to 3, wherein at least a part of the plurality of dented units includes, in the first surface of the bottom portion, one or a plurality of recessed portions.

In the nonwoven fabric, since at least a part of the plurality of dented units includes, in the first surface of the bottom portion, one or a plurality of recessed portions, the surface area of the nonwoven fabric with which the housing space of the dented units comes in contact is increased, and it is easier to let the highly viscous excrement which is housed in the housing space of the dented units permeate from the first surface to the second surface. Further, the recessed portion functions as the spacer between the layer adjacent on the second surface side (for example, an absorbent body), and it is difficult for the highly viscous excrement which has permeated the nonwoven fabric to return to the nonwoven fabric.

[Aspect 5]

The nonwoven fabric according to aspect 4, wherein the one or the plurality of recessed portions are disposed in a peripheral portion in the bottom portion which is adjacent to the first ridge portions and/or the second ridge portions, and in the first ridge portions and/or the second ridge portions, a fiber density of an adjacent portion which is adjacent to the one or the plurality of recessed portions is lower than a fiber density of a non-adjacent portion which is not adjacent to the one or the plurality of recessed portions.

In the first ridge portion and/or the second ridge portion of the nonwoven fabric, since the fiber density of the adjacent portion is lower than the fiber density of the non-adjacent portion, it is easier for the dented units to let the highly viscous excrement which is housed in the housing space thereof permeate from the first surface to the second surface through the adjacent portion.

[Aspect 6]

The nonwoven fabric according to aspect 4 or 5, wherein at least a part of the one or the plurality of recessed portions includes a penetration hole.

In the nonwoven fabric, since at least a part of the one or the plurality of recessed portions include a penetration hole, it is easier for the dented units to let the highly viscous excrement which is housed in the housing space thereof permeate from the first surface to the second surface through the penetration hole.

[Aspect 7]

The nonwoven fabric according to any one of aspects 1 to 6, wherein at least a part of the plurality of dented units includes, in the first surface of the bottom portion, a third ridge portion which extends in the first direction and is connected to the two second ridge portions, and a height of the first ridge portions is larger than a pitch of the first ridge portions and the third ridge portion.

In at least a part of the plurality of dented units of the nonwoven fabric, since the height of the first ridge portion is larger than the pitch of the first ridge portion and the third ridge portion, in a case in which a first ridge portion collapses in the second direction by body pressure of the wearer, etc., the first ridge portion is to be in a state of leaning on the third ridge portion, whereby the third ridge portion can support the first ridge portion, and it is easier for the first ridge portion to return to the original position. Accordingly, it is difficult for the first ridge portion to block the housing space of the dented units, and for the housing of the highly viscous excrement by the housing space of the dented units to be hindered.

[Aspect 8]

The nonwoven fabric according to any one of aspects 1 to 7, wherein the each of the plurality of second ridge portions extends along the second direction.

In the nonwoven fabric, since each of the second ridge portions extends along the second direction, even in a case in which body pressure of the wearer, etc., is applied to the nonwoven fabric, the plurality of second ridge portion which are disposed in the second direction so as to be orthogonal to the plurality of first ridge portion which extend in the first direction can support the first ridge portions, whereby it is difficult for the first ridge portions to be crushed in the thickness direction. Further, in the nonwoven fabric, since each of the plurality of second ridge portions is disposed along the second direction, when body pressure, etc., so as to compress the nonwoven fabric in the second direction is applied thereto, it is difficult for the nonwoven fabric to be crushed in the second direction. Accordingly, in such a case, it is difficult for the highly viscous excrement which is housed in the housing space of the dented units to overflow from the dented units.

[Aspect 9]

The nonwoven fabric according to any one of aspects 1 to 8, wherein the each of the plurality of dented units has a predetermined first direction length and a predetermined second direction length, and the plurality of dented units are disposed continuously in the first direction, with positions in the second direction being aligned.

In the nonwoven fabric, since the plurality of dented units, each having the same size, are disposed continuously in the first direction, with positions in the second direction being aligned, the nonwoven fabric has an excellent appearance, and can visually appeal the above-described effect to the user, for example, the wearer or the caregiver.

[Aspect 10]

The nonwoven fabric according to any one of aspects 1 to 9, wherein the nonwoven fabric includes, in the second surface, a plurality of first ridge portion corresponding groove portions each of which being overlapped with the each of the plurality of first ridge portions in the thickness direction.

Since the nonwoven fabric includes, in the second surface, the predetermined first ridge portion corresponding groove portions, it is easier for each of the plurality of dented units to let the highly viscous excrement which is housed in the housing space thereof permeate, in the first ridge portion (especially the first side surface of the first ridge portion), from the first surface to the second surface.

[Aspect 11]

The nonwoven fabric according to any one of aspects 1 to 9, wherein the nonwoven fabric includes, in the second surface, a plurality of second ridge portion corresponding groove portions each of which being overlapped with the each of the plurality of second ridge portions in the thickness direction.

Since the nonwoven fabric includes, in the second surface, the predetermined second ridge portion corresponding groove portions, it is easier for each of the plurality of dented units to let the highly viscous excrement which is housed in the housing space thereof permeate, in the second ridge portion (especially the second side surface of the second ridge portion), from the first surface to the second surface.

[Aspect 12]

The nonwoven fabric according to any one of aspects 4 to 6, wherein the at least the part of the plurality of dented units includes, in the second surface of the bottom portion, one or a plurality of protruded portions each of which being overlapped with the one or the plurality of recessed portions in the thickness direction.

In the nonwoven fabric, since at least a part of the plurality of dented units includes the predetermined protruded portions, it is easier to let the highly viscous excrement which is housed in the housing space of the dented units permeate from the first surface to the second surface through the recessed portions. Further, it is easier for the recessed portions to function as the spacer between the layer adjacent on the second surface side (for example, an absorbent body).

[Aspect 13]

The nonwoven fabric according to aspect 7, wherein the nonwoven fabric includes, in the second surface, a plurality of third ridge portion corresponding groove portions each of which being overlapped with each of a plurality of the third ridge portions in the thickness direction.

Since the nonwoven fabric includes, in the second surface, the predetermined third ridge portion corresponding groove portions, it is easier for each of the plurality of dented units to let the highly viscous excrement which is housed in the housing space thereof permeate, in the third ridge portion (especially the third side surface of the third ridge portion), from the first surface to the second surface.

Hereinbelow, the nonwoven fabric for an absorbent article according to the present disclosure is explained in detail. Incidentally, hereinbelow, "the nonwoven fabric for an absorbent article" may be referred to simply as "the nonwoven fabric".

[The Nonwoven Fabric According to the First Embodiment]

Figure 2:
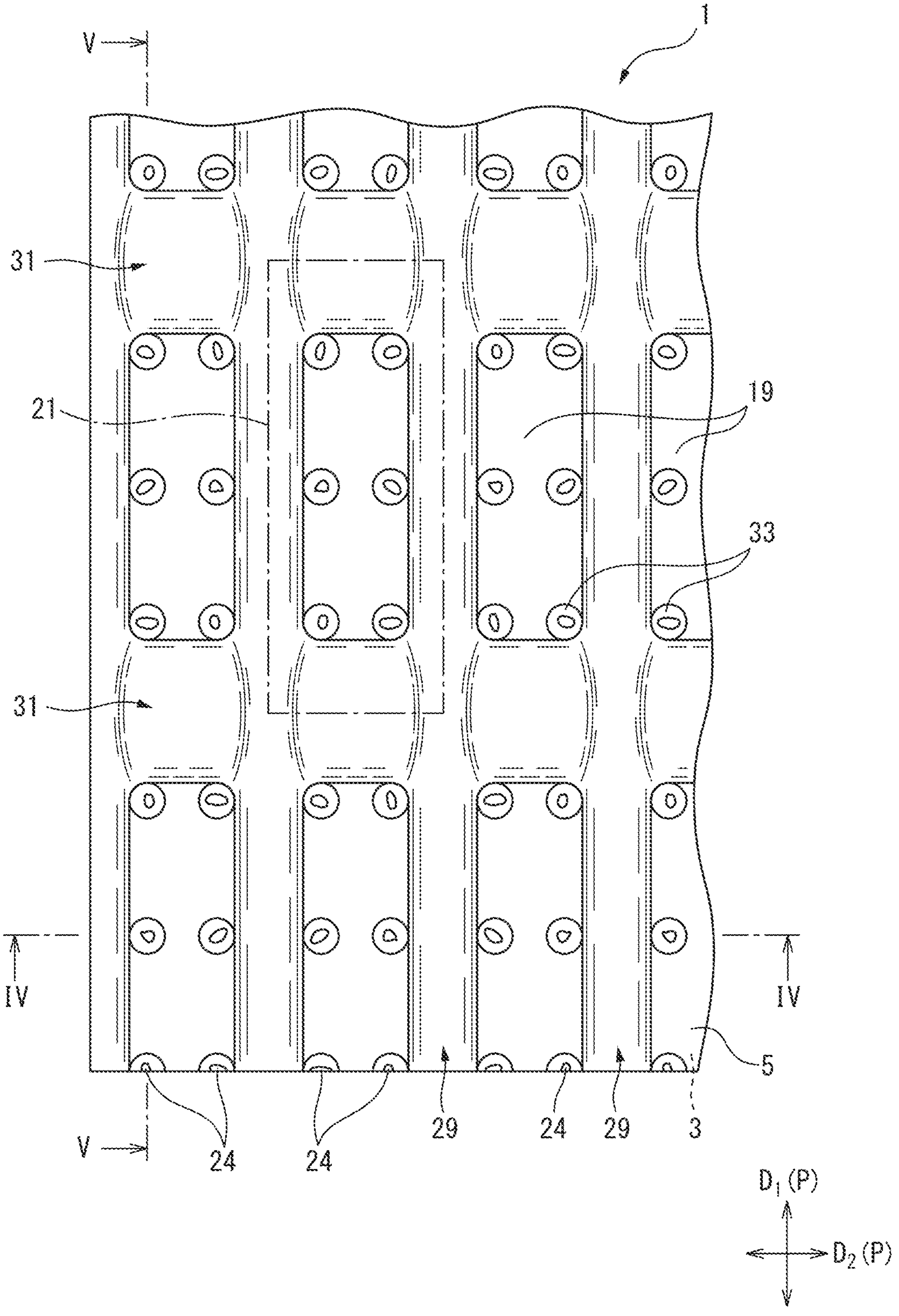
FIG. 2 is a plan view of the nonwoven fabric 1 according to the first embodiment on the second surface 5 side.
Figure 3:
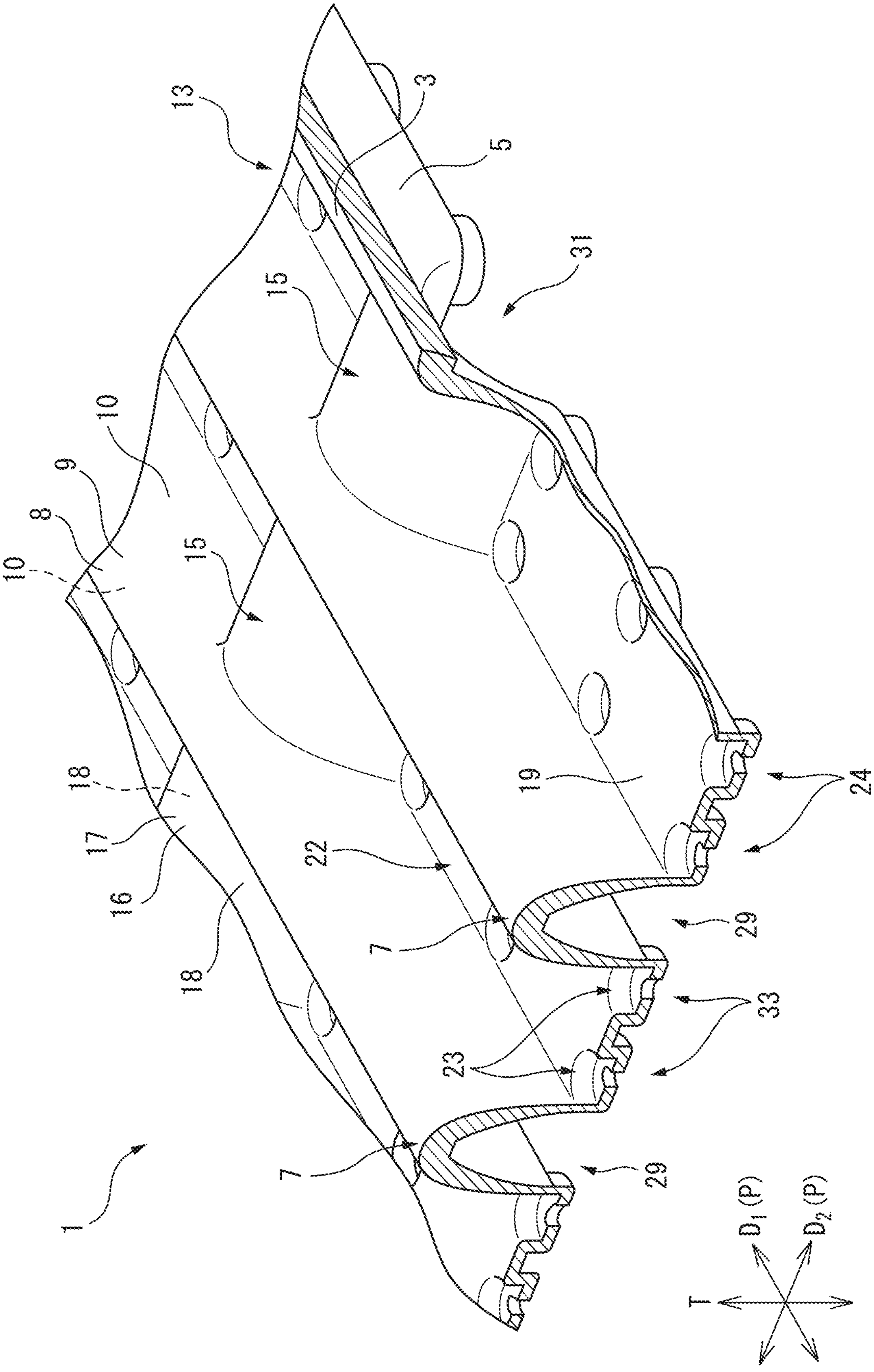
FIG. 3 is a perspective view of the nonwoven fabric 1 according to the first embodiment on the first surface 3 side.
Figure 4:
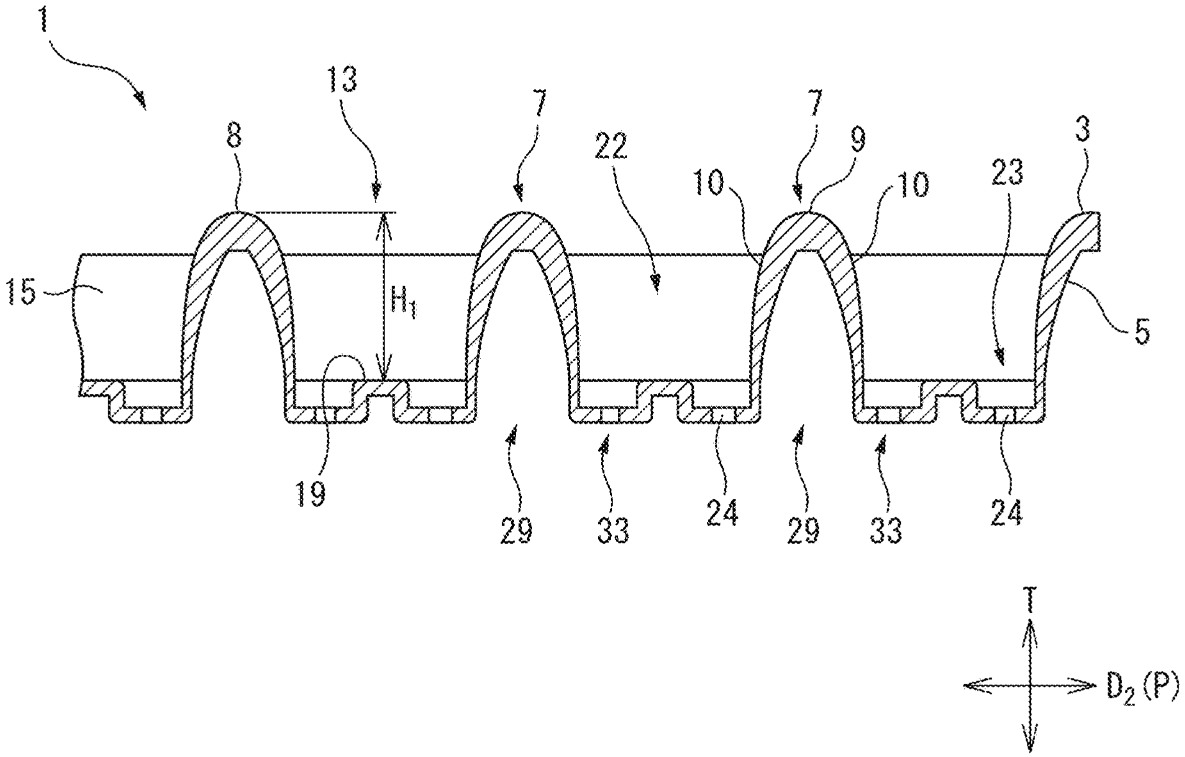
FIG. 4 is a sectional view at a IV-IV sectional surface of FIG. 1 and FIG. 2.
Figure 5:
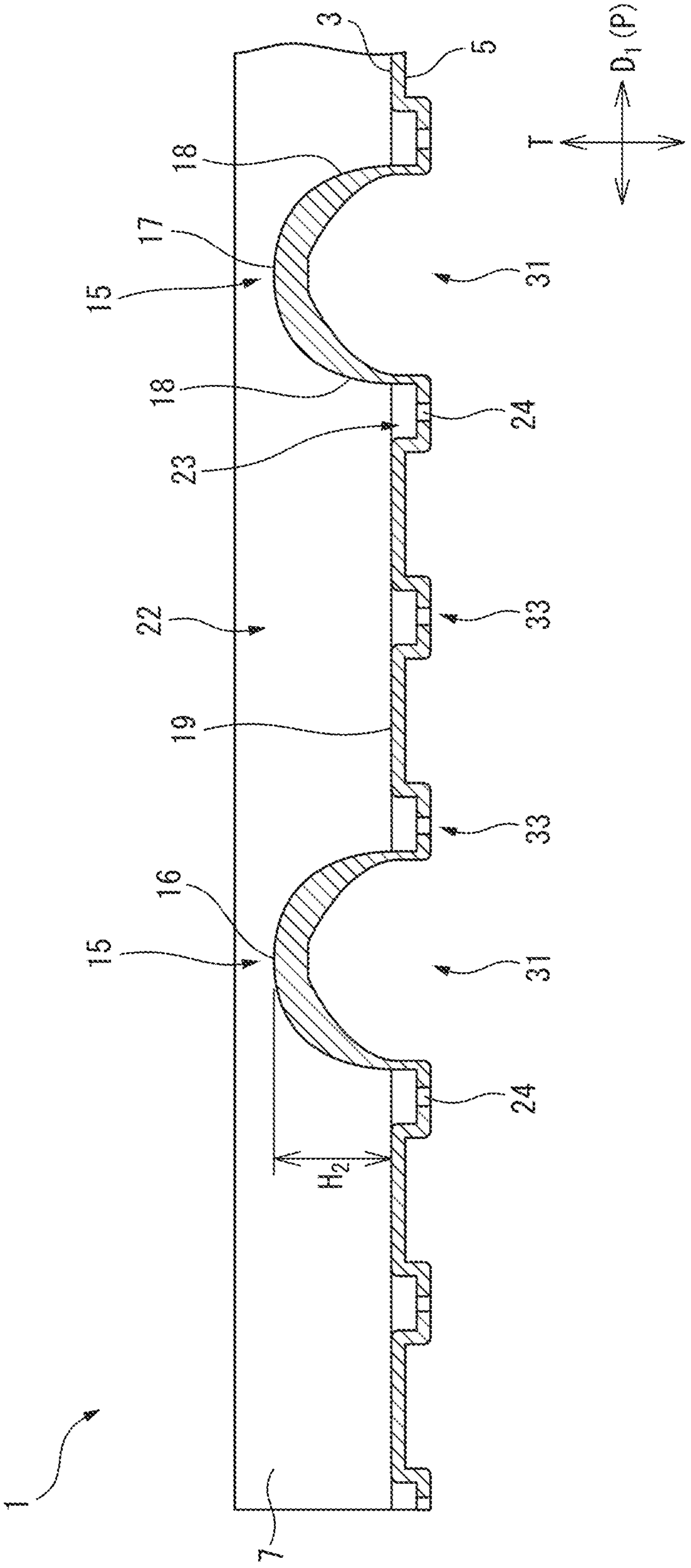
FIG. 5 is a sectional view at a V-V sectional surface of FIG. 1 and FIG. 2.

FIG. 1 and FIG. 2 are plan views of the nonwoven fabric 1 according to one embodiment of the present disclosure (hereinbelow, which is referred to as "the first embodiment") on the first surface 3 side, and on the second surface 5 side, respectively. FIG. 3 is a perspective view of the nonwoven fabric 1 according to the first embodiment on the first surface 3 side. FIG. 4 and FIG. 5 are sectional views at a IV-IV sectional surface and a V-V sectional surface, respectively, of FIG. 1 and FIG. 2.

The nonwoven fabric 1 according to the first embodiment includes the first surface 3 and the second surface 5, and further includes the plane direction P that includes the first direction $D_1$ and the second direction $D_2$ orthogonal to the first direction $D_1$, and the thickness direction T. Incidentally, the first direction $D_1$, the second direction $D_2$, and the thickness direction T are mutually orthogonal to each other. Further, the plane direction P and the thickness direction T are orthogonal to each other.

The nonwoven fabric 1 includes the plurality of first ridge portions 7 which extend in the first direction $D_1$, and the plurality of first groove portions 13 which extend in the first direction $D_1$. Incidentally, the first ridge portions 7 and the first groove portions 13 are alternately disposed in the second direction $D_2$. Each of the plurality of first ridge portions 7 is, in the first surface 3, protruded in the thickness direction T. In other words, each of the plurality of first ridge portions 7 is protruded in the thickness direction T, in the direction from the second surface 5 toward the first surface 3. Further, each of the plurality of first groove portions 13 is, in the first surface 3, recessed in the thickness direction T. In other words, each of the plurality of second ridge portions 15 is recessed in the thickness direction T, in the direction from the first surface 3 toward the second surface 5.

Each of the plurality of first ridge portions 7 includes the first top portion 8, and each of the plurality of first ridge portions 7 is partitioned into the first top surface 9 that includes the first top portion 8, and the two first side surfaces 10 which are disposed on both outer sides in the second direction $D_2$ with the first top surface 9 as the center.

Each of the plurality of first groove portions 13 includes the plurality of second ridge portions 15 and the plurality of bottom portions 19. The second ridge portions 15 and the bottom portions 19 are alternately disposed in the first direction $D_1$. Each of the plurality of second ridge portions 15 is, in the first surface 3, protruded in the thickness direction T, and is connected to two adjacent first ridge portions 7.

Each of the plurality of second ridge portions 15 is disposed along the second direction $D_2$, and the plurality of second ridge portions 15 are continuously disposed in the second direction with the plurality of first ridge portions 7 in between. In other words, the plurality of first ridge portions 7 and the plurality of second ridge portions 15 are disposed in a lattice pattern, and the later-described dented unit 21 configures each lattice.

Each of the plurality of second ridge portions 15 includes the second top portion 16, and each of the plurality of second ridge portions 15 is partitioned into the second top surface 17 that includes the second top portion 16, and the two second side surfaces 18 which are disposed on both outer sides in the first direction $D_1$ with the second top surface 17 as the center.

The nonwoven fabric 1 is configured by the plurality of dented units 21. Each of the plurality of dented units 21 is partitioned by two virtual surfaces which pass through the first top portions 8 of the two first ridge portions 7 being adjacent to a bottom portion 19, with the bottom portion 19 as the center, and which extend in the thickness direction T, and two virtual surfaces (which are not shown) which pass through the second top portions 16 of the two second ridge portions 15 being adjacent to such a bottom portion 19, and which extend in the thickness direction T.

In each of the plurality of dented units 21, the housing space 22 which houses the highly viscous excrement is formed by two first ridge portions 7 (especially, the first side surfaces 10 of the two first ridge portions 7), two second ridge portions 15 (especially, the second side surfaces 18 of the two second ridge portions 15), and the bottom portion 19.

The plurality of dented units 21 include the predetermined first direction length $L_1$ and the predetermined second direction length $L_2$, that is, each of the plurality of dented units 21 has the same size, and the plurality of dented units 21 having the same size are disposed continuously in the first direction $D_1$, with positions in the second direction $D_2$ being aligned. According to such a configuration, the nonwoven fabric 1 has an excellent appearance, and can visually appeal the effect of the present disclosure to the user, for example, the wearer or the caregiver.

In each of the plurality of dented units 21, heights of the two first ridge portions 7 are higher than heights of the two second ridge portions 15. According to such a configuration, it is difficult for the two second ridge portions 15 to be crushed due to it being difficult to receive influence of body pressure, etc., and it is also difficult for the first ridge portions 7 which are supported by the two second ridge portions 15 to be crushed.

In each of the plurality of dented units 21, the fiber density (which is not shown) of the first side surfaces 10 of the first ridge portions 7 is lower than the fiber density (which is not shown) of the first top surface 9 of the first ridge portions 7. Further, in each of the plurality of dented units 21, the fiber density (which is not shown) of the second side surfaces 18 of the second ridge portions 15 is lower than the fiber density (which is not shown) of the second top surface 17 of the second ridge portions 15. According to such a configuration, each of the plurality of dented units 21 can let the highly viscous excrement (which is not shown) which is housed in the housing space 22 thereof permeate from the first surface 3 to the second surface 5 through the first side surfaces 10 and the second side surfaces 18, can make the volume of the housed highly viscous excrement (which is not shown) smaller, and can separate the highly viscous excrement (which is not shown) which is housed in the plurality of dented units 21 from the wearer.

In the nonwoven fabric 1 according to the first embodiment, each of the plurality of dented units 21 includes, in the bottom portions 19, six recessed portions 23 which are recessed in the thickness direction T in the first surface 3, and the six recessed portions include penetration holes 24 which penetrate from the first surface 3 to the second surface 5. According to such a configuration, it is easier for the dented units 21 to let the highly viscous excrement (which is not shown) which is housed in the housing space 22 thereof permeate from the first surface 3 to the second surface 5 through the penetration holes 24.

In each of the plurality of dented units 21, the six recessed portions 23 are disposed at the peripheral portion of a bottom portion 19, and the fiber density of the adjacent portion (which is not shown) of a first ridge portion 7 (to be more specific, the first side surfaces 10 thereof) and a second ridge portion 15 (to be more specific, the second side surfaces 18 thereof), adjacent to a recessed portion 23, is lower than the fiber density of the non-adjacent portion (which is not shown) which is not adjacent to the recessed portion. According to such a configuration, it is easier for the dented units 21 to let the highly viscous excrement (which is not shown) which is housed in the housing space 22 thereof permeate from the first surface 3 to the second surface 5 through the adjacent portion (which is not shown).

The nonwoven fabric 1 according to the first embodiment includes, in the second surface 5, the plurality of first ridge portion corresponding groove portions 29 and the plurality of second ridge portion corresponding groove portions 31. Each of the plurality of first ridge portion corresponding groove portions 29 is overlapped with each of the plurality of first ridge portions 7 in the thickness direction T, and is recessed in the thickness direction T in the second surface 5. Further, each of the plurality of second ridge portion corresponding groove portions 31 is overlapped with each of the plurality of second ridge portions 15 in the thickness direction T, and is recessed in the thickness direction T in the second surface 5. Each of the plurality of second ridge portion corresponding groove portions 31 is connected to two adjacent first ridge portion corresponding groove portions 29.

According to such a configuration, it is easier for each of the plurality of dented units 21 to let the highly viscous excrement (which is not shown) which is housed in the housing space 22 thereof permeate, in the first ridge portions 7 (especially, the first side surfaces 10 of the first ridge portions 7) and the second ridge portions 15 (especially, the second side surfaces 18 of the second ridge portions 15), from the first surface 3 to the second surface 5, and the permeated highly viscous excrement can be transferred to the layer which is present directly underneath, for example, the absorbent body.

Figure 6:
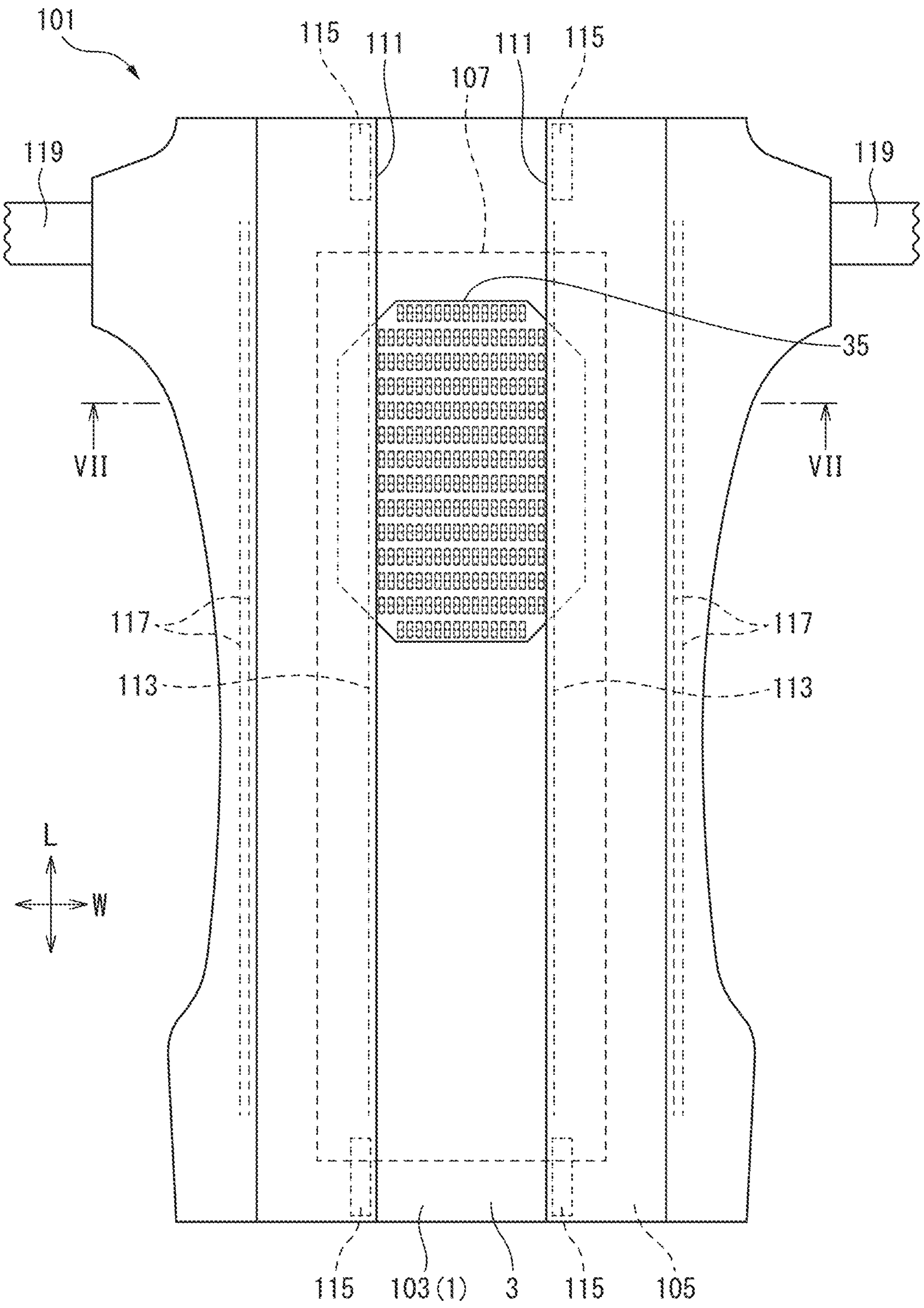
FIG. 6 is a plan view of the absorbent article 101 which includes the nonwoven fabric 1 according to the first embodiment as the liquid permeable sheet 103.
Figure 7:
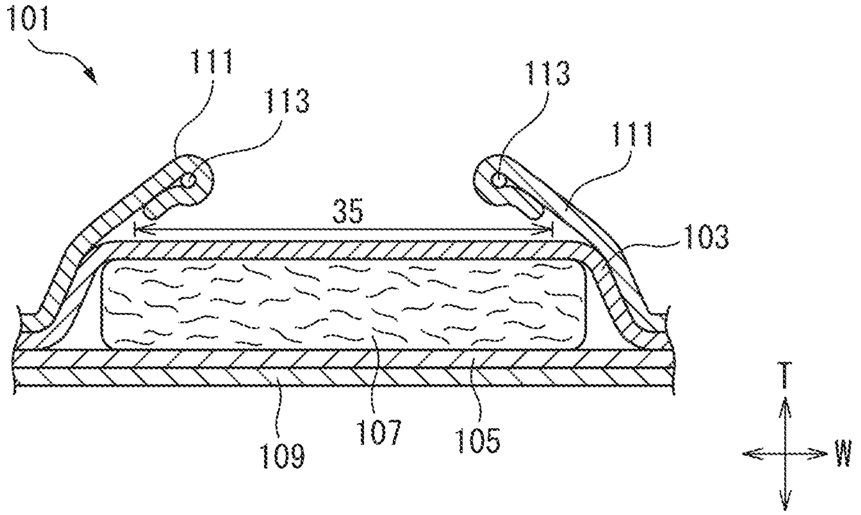
FIG. 7 is a sectional view at a VII-VII sectional surface of FIG. 6.

FIG. 6 is a plan view of the absorbent article 101, and to be more specific, a disposable diaper, which includes the nonwoven fabric 1 according to the first embodiment as the liquid permeable sheet 103. FIG. 7 is a sectional view at a VII-VII sectional surface of FIG. 6.

The absorbent article 101 includes the liquid permeable sheet 103, the liquid impermeable sheet 105, the absorbent body 107, and the exterior sheet 109, in this order. Further, the absorbent article 101 includes the longitudinal direction L, the width direction W, and the thickness direction T. Still further, the absorbent article 101 includes a pair of leakage barriers 111 that include elastic members 113, fixed portions 115 so as to fix the leakage barriers 111 to the liquid permeable sheet 103, elastic members 117, tape fasteners 119, etc.

The absorbent article 101 includes, in a part of the liquid permeable sheet 103, the dented unit region 35 which is configured by the plurality of dented units (which is not shown). The dented unit region 35 is disposed at the region which is to be in contact with the anus of the wearer when being worn, and more specifically at the region which overlaps with absorbent body 107 in the thickness direction T, in the rear side region than the center in the longitudinal direction L. Incidentally, in the dented unit region 35 shown in FIG. 6, only the bottom portions 19 of the plurality of dented units are shown for convenience, and in the dented unit region 35 shown in FIG. 7, the plurality of dented units themselves are not shown.

In the dented unit region 35, the plurality of dented units (which is not shown) are disposed so that the first surface (which is not shown) configures the skin contact surface, and the first direction (which is not shown) and the second direction (which is not shown) match the longitudinal direction L and the width direction W of the absorbent article 101, respectively.

Figure 8:
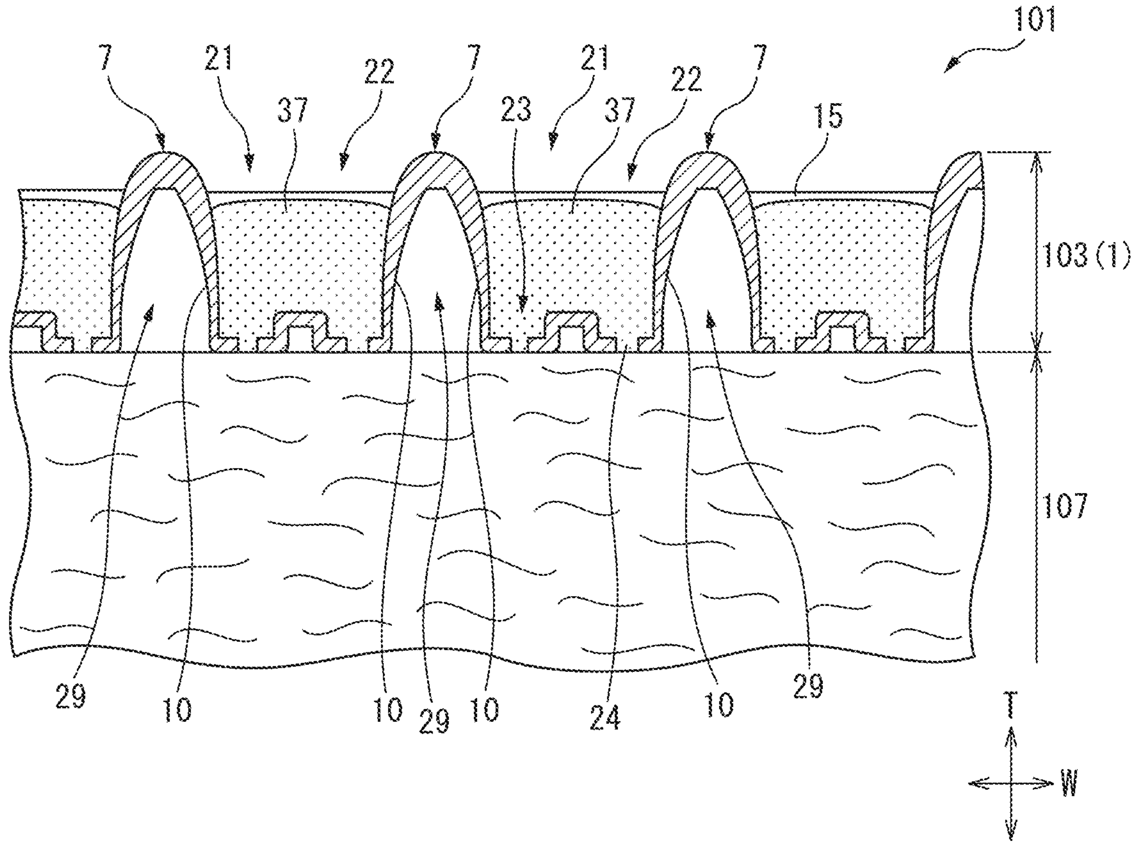
FIG. 8 is a view to explain the movement of the highly viscous excrement which is temporarily housed by the liquid permeable sheet 103 in the housing space 22, to the absorbent body 107.

FIG. 8 corresponds to a partial enlarged view of FIG. 7, and is a view to explain the movement of the highly viscous excrement 37 which is temporarily housed by the liquid permeable sheet 103 in the housing space 22, to the absorbent body 107. The highly viscous excrement 37 excreted by the wearer, for example, loose stool, is temporarily housed in each of the housing spaces 22 of the plurality of dented units 21, and is separated from the skin of the wearer.

Incidentally, in the liquid permeable sheet 103 (the nonwoven fabric 1), since the heights of the second ridge portions 15 are lower than the heights of the first ridge portions 7, in a case in which the highly viscous excrement 37 with an amount which cannot be temporarily accommodated by a dented unit 21 reaches the dented unit 21, the highly viscous excrement 37 is moved to the dented unit 21 adjacent in the longitudinal direction (the first direction) beyond the second ridge portion 15, whereby the height of the highly viscous excrement 37 which is housed in the liquid permeable sheet 103 can be made to be lower than the height of the first ridge portions 7.

The highly viscous excrement 37 which is temporarily housed in the housing space 22 of the dented units 21 can move to the absorbent body 107 by passing through the penetration holes 24 of the recessed portions 23. Further, the highly viscous excrement 37 can move to the absorbent body, by permeating through (i) the wall surface of the recessed portions 23, (ii) the first side surfaces 10 of the first ridge portions 7, in which the fiber density is low, and (iii) the second side surfaces (which are not shown) of the second ridge portions, in which the fiber density is low. Still further, the recessed portions 23 of the dented units 21 function as the spacer between the absorbent body 107, and there is a tendency that it is difficult for the highly viscous excrement, moisture, etc., which have been absorbed by the absorbent body 107 to return to the liquid permeable sheet 103.

[The Nonwoven Fabric According to the Second Embodiment]

Figure 9:
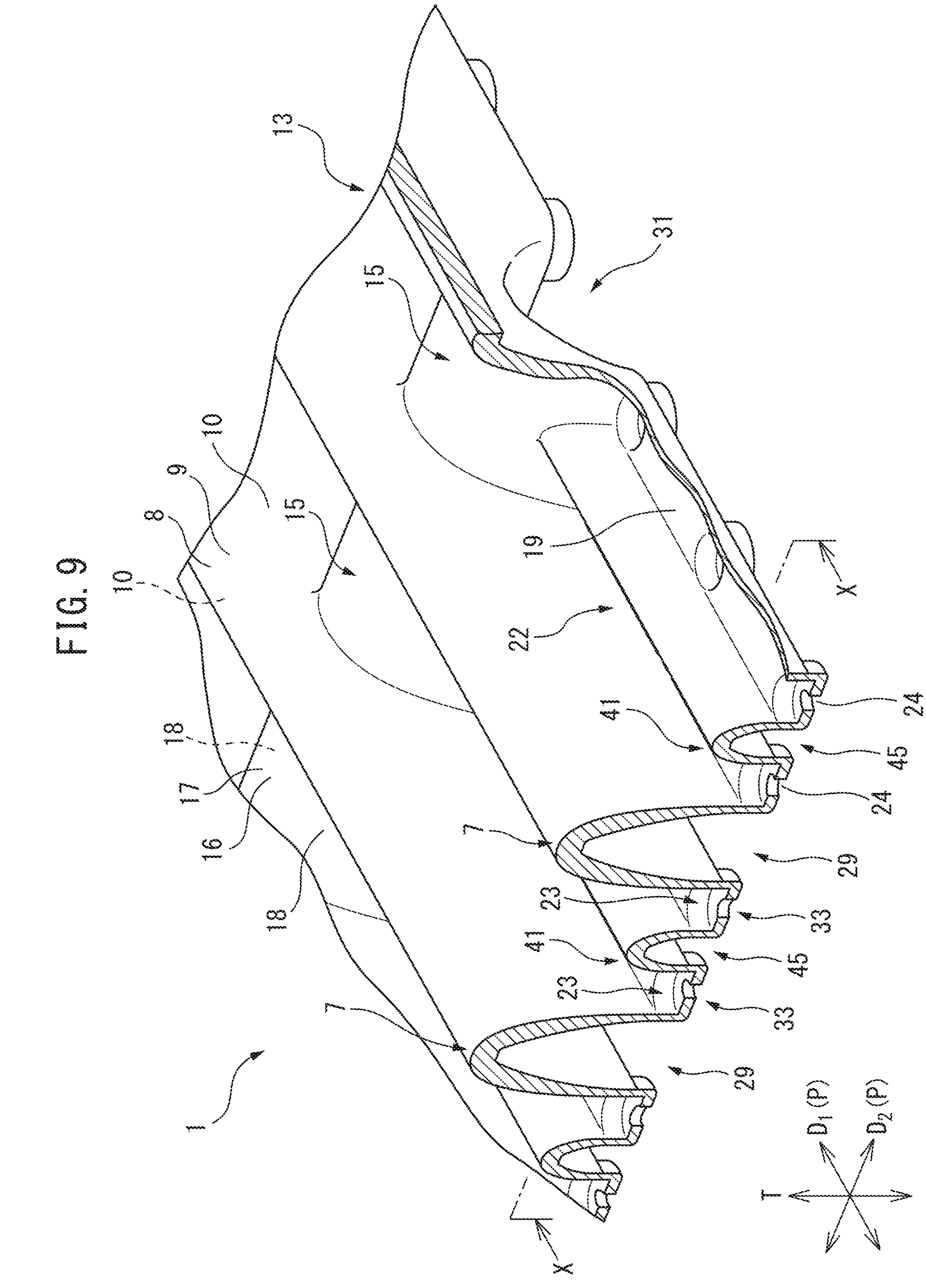
FIG. 9 is a perspective view of the nonwoven fabric 1 according to the second embodiment.
Figure 10:
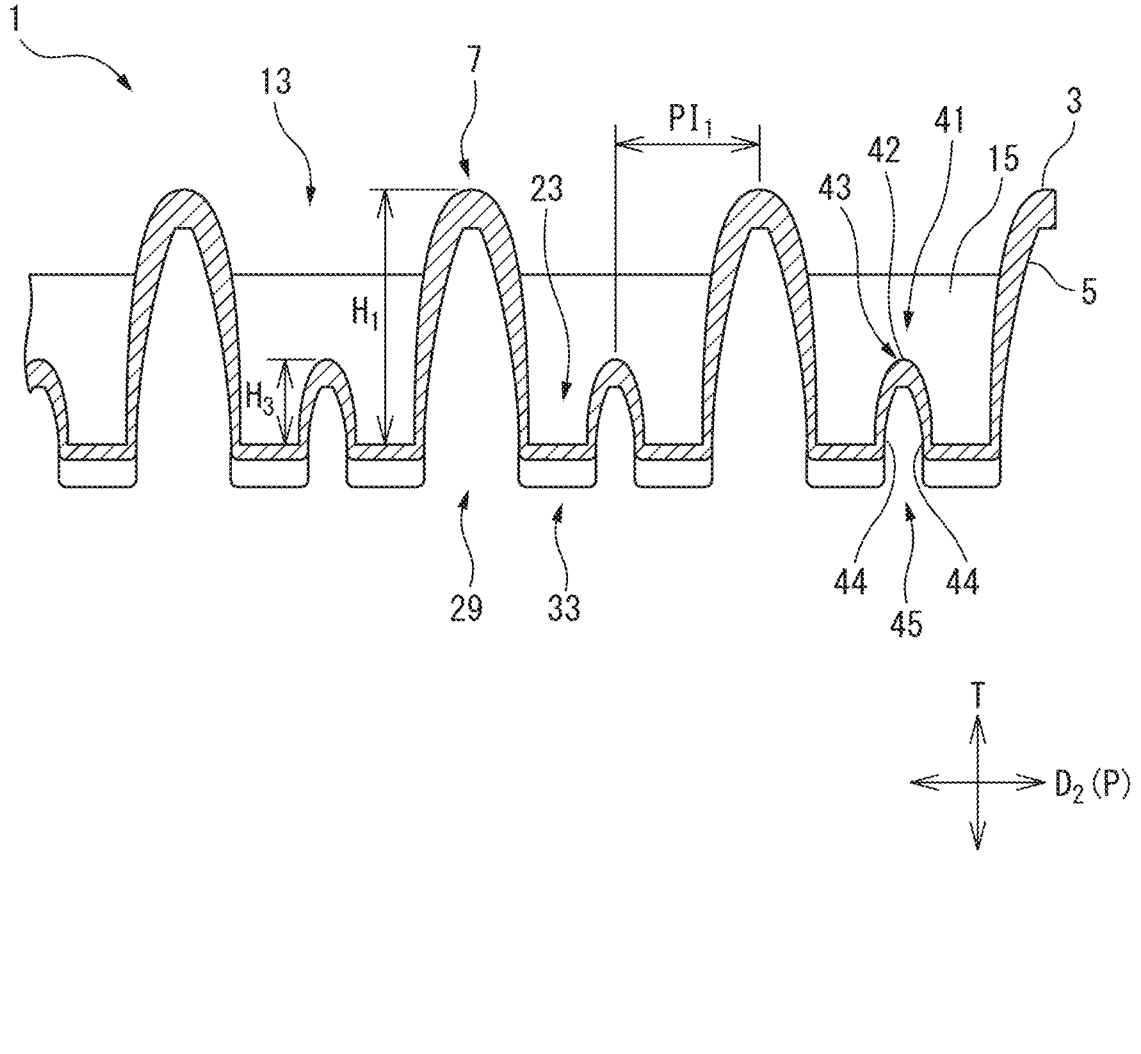
FIG. 10 is a sectional view at a X-X sectional surface of FIG. 9.

FIG. 9 and FIG. 10 are views so as to explain the nonwoven fabric 1 according to another embodiment of the present disclosure (hereinbelow, which is referred to as "the second embodiment"), and FIG. 9 is a perspective view, and FIG. 10 is a sectional view at a X-X sectional surface of FIG. 9.

The nonwoven fabric 1 according to the second embodiment includes, in each of the plurality of dented units (which are not shown), the third ridge portion 41 which protrudes in the thickness direction T in the first surface 3 of the bottom portions 19. The third ridge portion 41 extends in the first direction $D_1$ and is connected to two adjacent second ridge portions 15. The height $H_3$ of the third ridge portion 41 is lower than the height $H_1$ of the first ridge portions 7 and the height (which is not shown) of the second ridge portions 15. Further, the height $H_1$ of the first ridge portions 7 is larger than the pitch PI) of the first ridge portion and the third ridge portion. According to such a configuration, in a case in which a first ridge portion 7 collapses in the second direction $D_2$ by body pressure of the wearer, etc., the first ridge portion 7 is to be in a state of leaning on the third ridge portion 41, whereby the third ridge portion 41 can support the first ridge portion 7, and it is easier for the first ridge portion 7 to return to the original position.

The nonwoven fabric 1 according to the second embodiment includes, in each of the plurality of dented units 21, the third ridge portion corresponding groove portion 45 in the second surface. The third ridge portion corresponding groove portion 45 overlaps with the third ridge portion 41 in the thickness direction T, and is recessed in the thickness direction T in the second surface 5. Further, the third ridge portion corresponding groove portion 45 is connected to two second ridge portion corresponding groove portions 31.

The portions other than the third ridge portions 41 are the same as those in the first embodiment, and thus, the explanation thereof is omitted.

[The Nonwoven Fabric According to the Third Embodiment]

Figure 11:
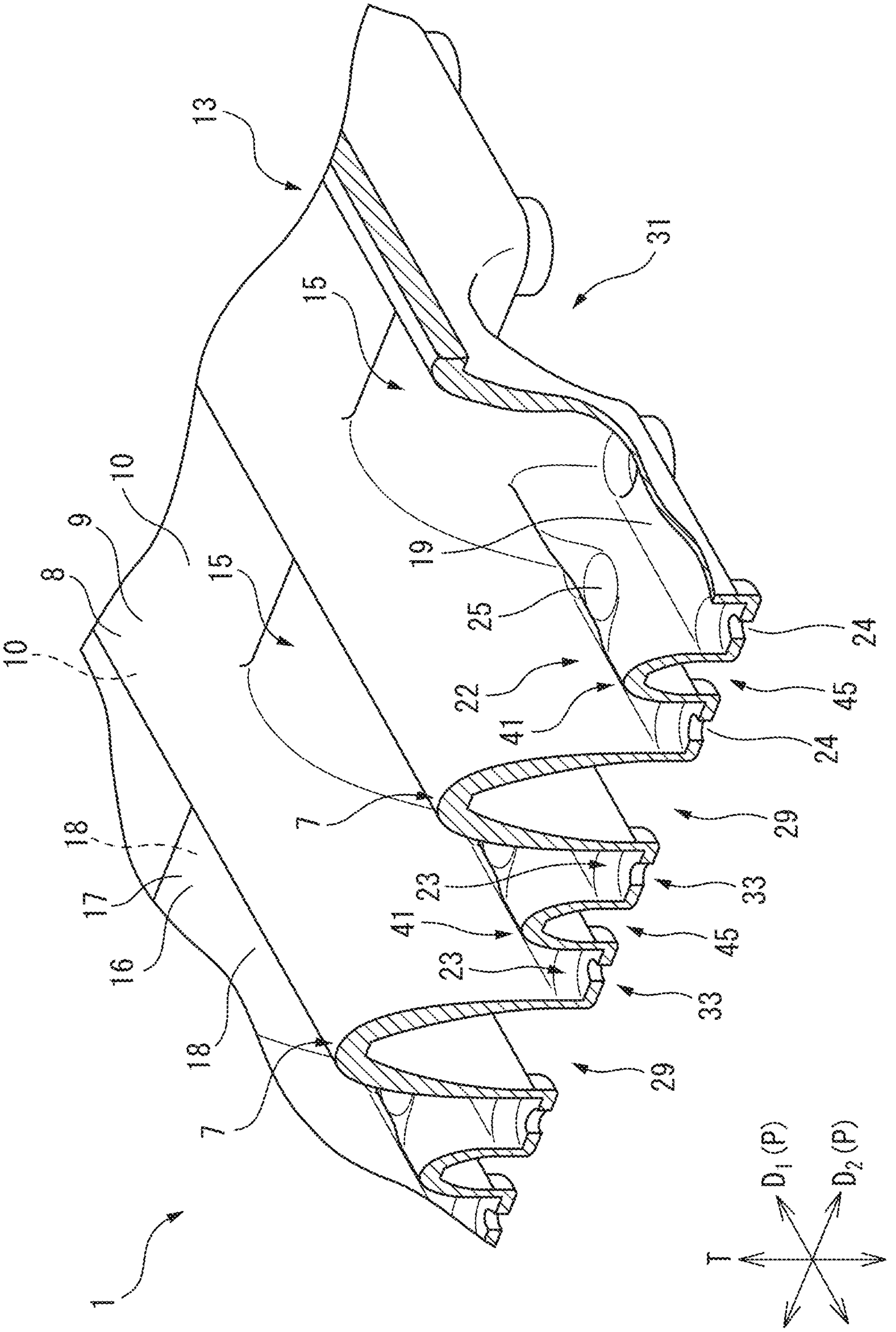
FIG. 11 is a perspective view of the nonwoven fabric 1 according to the third embodiment.

FIG. 11 is a view so as to explain the nonwoven fabric 1 according to another embodiment of the present disclosure (hereinbelow, which is referred to as "the third embodiment"), and is a perspective view.

The nonwoven fabric 1 according to the third embodiment includes, in each of the plurality of dented units (which are not shown), four recessed portions 23 which are recessed in the thickness direction T, in the first surface 3 of a bottom portion 19.

Further, the nonwoven fabric 1 according to the third embodiment includes, in each of the plurality of dented units (which are not shown), the third ridge portion 41 that includes the recessed portion 25 which is protruded in the thickness direction T while being recessed in the thickness direction T at the center in the first direction $D_1$, in the first surface 3 of a bottom portion 19. According to such a configuration, by letting the center in the first direction $D_1$ of the third ridge portion 41 be recessed, it is difficult for the third ridge portion 41 to be crushed by the body pressure of the wearer, etc., and for the first ridge portions 7 to be crushed.

The other portions are the same as those in the first embodiment, and thus, the explanation thereof is omitted.

[The Nonwoven Fabric According to the Fourth Embodiment]

Figure 12:
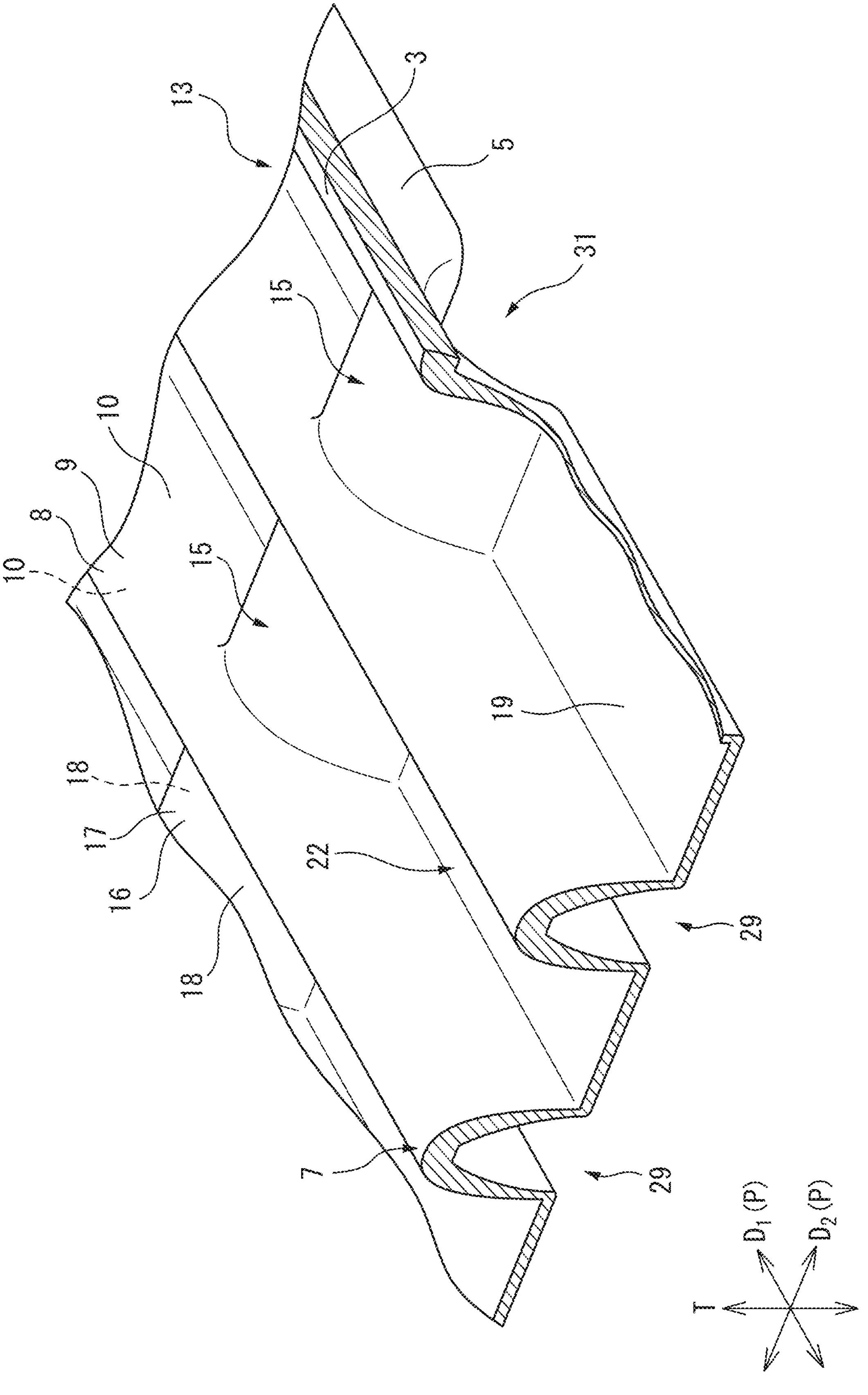
FIG. 12 is another perspective view of the nonwoven fabric 1 according to the third embodiment.

FIG. 12 is a view so as to explain the nonwoven fabric 1 according to another embodiment of the present disclosure (hereinbelow, which is referred to as "the fourth embodiment"), and is a perspective view.

In the nonwoven fabric 1 according to the fourth embodiment, the recessed portions are not present in a bottom portion 19, in each of the plurality of dented units 21. According to such a configuration, in a case in which the nonwoven fabric 1 is used, for example, as the liquid permeable sheet of an absorbent article, so that the first surface 3 configures the skin contact surface, it is easier for the bottom portions 19 to be in direct contact with the absorbent body, whereby it is easier to move the highly viscous excrement which is housed in the housing space 22 of the dented units 21 to the absorbent body through the bottom portions 19.

The other portions are the same as those in the first embodiment, and thus, the explanation thereof is omitted.

In the nonwoven fabric according to the present disclosure, the first ridge portion, as shown in the first embodiment to the fourth embodiment, may be extended continuously in the first direction, or may be extended intermittently in the first direction, for example, may include a portion in which the height thereof is partially low. According to such a configuration, a dented unit can deliver the highly viscous excrement which is housed in the housing space thereof to the dented unit adjacent in the second direction, whereby it is easier for the skin of the wearer of the absorbent article and the highly viscous excrement which is housed in the dented unit to be separated.

In the nonwoven fabric according to the present disclosure, the first ridge portion has a height preferably of 0.5 to 4.0 mm, and more preferably of 1.0 to 3.0 mm. This is from the viewpoint of securing the housing space of the dented units and the difficulty of the first ridge portion to be crushed. Further, in the nonwoven fabric according to the present disclosure, the first ridge portion has a width (the second direction length) preferably of 0.3 to 2.5 mm, and more preferably of 0.5 to 1.5 mm. This is from the viewpoint of the difficulty of the first ridge portion to be crushed. Still further, in the nonwoven fabric according to the present disclosure, the first ridge portion has a pitch preferably of 1.0 to 5.0 mm, and more preferably of 2.0 to 4.0 mm. This is from the viewpoint of securing the housing space of the dented units and separating the highly viscous excrement which is housed in the housing space of the dented units from the wearer.

The nonwoven fabric according to the present disclosure preferably includes the plurality of first ridge portion corresponding groove portions which overlap with the plurality of first ridge portion in the thickness direction of the nonwoven fabric and are recessed in the thickness direction in the second surface. This is from the viewpoint of the permeation property of the highly viscous excrement in the first ridge portions, especially in the first side surfaces of the first ridge portions. Further, the plurality of first ridge portion corresponding groove portions, in the second surface, preferably have no lid, that is, preferably have an opening portion. This is from the viewpoint of the permeation property of the highly viscous excrement.

In nonwoven fabric according to the present disclosure, in each of the plurality of dented units, the direction of the second ridge portion is not particularly limited as long as the second ridge portion extends in the direction crossing the first direction, however, the second ridge portion preferably extends along the second direction. This is from the viewpoint of the difficulty of the first ridge portion to be crushed in the thickness direction and of the difficulty of the nonwoven fabric to be crushed in the second direction, etc.

Further, in nonwoven fabric according to the present disclosure, in each of the plurality of dented units, the second ridge portion is preferably connected to at least one of the two adjacent first ridge portions, and is more preferably connected to both of the two adjacent first ridge portions. This is from the viewpoint of the effect of the present disclosure.

In nonwoven fabric according to the present disclosure, in each of the plurality of dented units, the second ridge portion may be extended continuously in the direction crossing the first direction, or may be extended intermittently in the direction crossing the first direction, for example, may include a portion in which the height thereof is partially low. According to such a configuration, a dented unit can deliver the highly viscous excrement which is housed in the housing space thereof to the dented unit adjacent in the first direction, whereby it is easier for the skin of the wearer of the absorbent article and the highly viscous excrement which is housed in the dented unit to be separated.

In the nonwoven fabric according to the present disclosure, the second ridge portion has a height preferably of 0.3 to 3.0 mm, and more preferably of 0.5 to 2.5 mm. This is from the viewpoint of securing the housing space of the dented units and the difficulty of the second ridge portion to be crushed. Further, in the nonwoven fabric according to the present disclosure, the second ridge portion has a width (the first direction length) preferably of 0.6 to 5.0 mm, and more preferably of 1.0 to 4.0 mm. This is from the viewpoint of supporting the first ridge portions. Still further, in the nonwoven fabric according to the present disclosure, the second ridge portion has a pitch preferably of 1.0 to 10.0 mm, and more preferably of 2.0 to 6.0 mm. This is from the viewpoint supporting the first ridge portions.

The second ridge portions preferably have lower heights than the first ridge portions. This is because it is difficult for the second ridge portions to be crushed due to it being difficult to receive influence of body pressure, etc., and it is also difficult for the first ridge portions which are supported by the second ridge portions to be crushed. Further, this is also because the highly viscous excrement which is housed in a housing space of a dented unit can be delivered to the dented unit adjacent in the first direction. Further, the second ridge portions preferably have wider widths than the first ridge portions. This is from the viewpoint of, by making the first ridge portions higher, while the dented units separating the highly viscous excrement which is housed in the housing spaces thereof and the skin of the wearer, supporting the first ridge portions in which it is easy for the strength thereof to be lowered, by the second ridge portions.

The nonwoven fabric according to the present disclosure preferably includes the plurality of second ridge portion corresponding groove portions which overlap with the plurality of second ridge portions in the thickness direction and are recessed in the thickness direction in the second surface. This is from the viewpoint of the permeation property of the highly viscous excrement in the second ridge portions, especially in the second side surfaces of the second ridge portions. Further, the plurality of second ridge portion corresponding groove portions, in the second surface, preferably have no lid, that is, preferably have an opening portion. This is from the viewpoint of the permeation property of the highly viscous excrement.

Further, in a case in which the nonwoven fabric according to the present disclosure has the first ridge portion corresponding groove portions, the second ridge portion corresponding groove portion, in each of the plurality of dented units, is preferably connected to at least one of the two adjacent first ridge portion corresponding groove portions, and is more preferably connected to both of the two adjacent first ridge portion corresponding groove portions. This is from the viewpoint of the effect of the present disclosure.

In the nonwoven fabric according to the present disclosure, in the plurality of dented units, the fiber density of the first side surfaces of the first ridge portions is preferably lower than the fiber density of the first top surface. This is from the viewpoint of the permeation property of the highly viscous excrement in the first side surfaces of the first ridge portions. Further, from the same viewpoint, in the plurality of dented units, the fiber density of the first side surfaces of the first ridge portions is preferably lower than the fiber density of the bottom portions.

Further, in the nonwoven fabric according to the present disclosure, in the plurality of dented units, the fiber density of the second side surfaces of the second ridge portions is preferably lower than the fiber density of the second top surface. This is from the viewpoint of the permeation property of the highly viscous excrement in the second side surfaces of the second ridge portions. Further, from the same viewpoint, in the plurality of dented units, the fiber density of the second side surfaces of the second ridge portions is preferably lower than the fiber density of the bottom portions.

Incidentally, the highs and lows of the fiber density can be determined by enlarging the corresponding portion (for example, with a size of 1 mm×1 mm) to approximately 100 times with an electron microscope, etc., and visually counting the number of fibers, etc.

In the nonwoven fabric according to the present disclosure, the recessed portions formed in the bottom portions are an optional requirement. In the nonwoven fabric according to the present disclosure, as shown in the first embodiment to the third embodiment, in a case in which at least a part of the plurality of dented units includes one or a plurality of recessed portions in a bottom portion, the one or the plurality of recessed portions are preferably disposed continuously or intermittently along the peripheral portion of the bottom portion. This is because, according to such a configuration, there is a tendency that the fiber density of the first side surfaces of the first ridge portions adjacent to the bottom portion and/or the second side surfaces of the second ridge portions adjacent thereto is lower compared to the case in which the one or the plurality of recessed portions are not present in the bottom portion. Further, there is also a tendency that it is easier for the recessed portions to include a penetration hole.

The depth of the recessed portions, that is, the height from the first surface of a bottom portion to the first surface of the bottom of a recessed portion, is preferably 0.05 to 0.5 mm, and is more preferably 0.1 to 0.3 mm. This is from the viewpoint of lowering the fiber density of the first side surfaces of the first ridge portions and of the second side surfaces of the second ridge portions.

The recessed portions preferably include a penetration hole, and more specifically, the recessed portions preferably include a penetration hole in a part of the recessed portions, and more preferably include a penetration hole in the whole recessed portions. This is from the viewpoint of letting the highly viscous excrement which is housed in the housing spaces of the dented units directly pass through, through the penetration hole.

In a case in which the recessed portions are disposed in the peripheral portions of the bottom portions, that is, in the peripheral portions of the bottom portions adjacent to the first side surfaces of the first ridge portions and/or the second side surfaces of the second ridge portions, the fiber density of the adjacent portion which is adjacent to the recessed portions among the first side surfaces of the first ridge portions and the second side surfaces of the second ridge portions, is preferably lower than the fiber density of the non-adjacent portion which is not adjacent to the recessed portions. This is from the viewpoint of the permeation property of the highly viscous excrement.

As the adjacent portion, portions which are adjacent to the recessed portions, of the first side surfaces of the first ridge portions and the second side surfaces of the second ridge portions may be mentioned, and as the non-adjacent portion, portions which are adjacent to the first top surface and the second top surface, in the first side surfaces of the first ridge portions and the second side surfaces of the second ridge portions, respectively, may be mentioned.

In the nonwoven fabric according to the present disclosure, the third ridge portions are an optional requirement. In the nonwoven fabric according to the present disclosure, as shown in the second embodiment and the third embodiment, in a case in which at least a part of the plurality of dented units includes the third ridge portions, the direction in which the third ridge portions extend is not particularly limited, however, the third ridge portions preferably extend along the first direction. This is because when a first ridge portion collapses in the second direction, it is easier for the first ridge portion to return to the original position. Further, a third ridge portion is preferably connected to at least one of two second ridge portions, and is more preferably connected to both of the two second ridge portions. This is because it is difficult for a second ridge portion to be crushed, and when a first ridge portion collapses in the second direction, it is easier for the first ridge portion to return to the original position. The third ridge portions may include a portion in which the height thereof is partially low.

The third ridge portion has a height preferably of 0.1 to 2.5 mm, and more preferably of 0.25 to 2.0 mm. This is from the viewpoint of the supporting the first ridge portions when collapsed in the second direction, securing the housing space of the dented units and the difficulty of the third ridge portion to be crushed. Further, the third ridge portion preferably has a lower height than a first ridge portion and a second ridge portion. This is because it is difficult for the third ridge portions to be crushed due to it being difficult to receive influence of body pressure, etc., and it is also difficult for the second ridge portions which are connected to the third ridge portions to be crushed, and for the first ridge portions which are connected to the second ridge portions to be crushed.

Further, the pitch between the first ridge portion and the third ridge portion is preferably 0.5 to 2.5 mm, and is more preferably 1.0 to 2.0 mm. Further, the pitch between the first ridge portion and the third ridge portion is preferably smaller than the height of the first ridge portion. This is because, in a case in which a first ridge portion collapses in the second direction by body pressure of the wearer, etc., the third ridge portion can support the first ridge portion, and it is easier for the first ridge portion to return to the original position.

In a case in which the nonwoven fabric according to the present disclosure includes, in at least a part of the plurality of dented units, the third ridge portions, the nonwoven fabric according to the present disclosure preferably includes the third ridge portion corresponding groove portions which overlap with the third ridge portion in the thickness direction and are recessed in the thickness direction in the second surface. This is from the viewpoint of the permeation property of the highly viscous excrement in the third ridge portions, especially in the third side surfaces of the third ridge portions. Further, the plurality of third ridge portion corresponding groove portions, in the second surface, preferably have no lid, that is, preferably have an opening portion. This is from the viewpoint of the permeation property of the highly viscous excrement.

Still further, in a case in which the nonwoven fabric according to the present disclosure includes the second ridge portion corresponding groove portions and the third ridge portion corresponding groove portions, the third ridge portion corresponding groove portion, in each of the plurality of dented units, is preferably connected to at least one of the two adjacent second ridge portion corresponding groove portions, and is more preferably connected to both of the two adjacent second ridge portion corresponding groove portions. This is from the viewpoint of the effect of the present disclosure.

The nonwoven fabric according to the present disclosure may include, in a whole or a part thereof, a dented unit region which is configured by the plurality of dented units. For example, among the nonwoven fabric, the dented unit region may be formed only in the place at which the highly viscous excrement comes in contact with the excretory opening.

In the dented unit region, the plurality of dented units each having the same size, that is, the same first direction length and the same second direction length are preferably arranged in a lattice pattern in the first direction and in the second direction. This is from the viewpoint of the nonwoven fabric having an excellent appearance, and of being capable of visually appealing the effect of the present disclosure to the user, for example, the wearer or the caregiver.

The nonwoven fabric according to the present disclosure may have a basis weight equivalent to that of a nonwoven fabric which is used for an absorbent article, especially as a liquid permeable sheet, and has a basis weight preferably of 10 to 50 $g/m^2$, and more preferably of 20 to 40 $g/m^2$.

In the present description, the basis weight is calculated by cutting out the nonwoven fabric so as to have an area of 100 $cm^2$, for example, in a size of 10 cm×10 cm, and measuring the mass thereof.

Further, the nonwoven fabric according to the present disclosure has a thickness preferably of 1.0 to 4.0 mm, and more preferably of 1.5 to 3.0 mm. This is from the viewpoint of the usage for an absorbent article. In other words, this is from the viewpoint of while maintaining the shape of the dented unit, letting the highly viscous excrement permeate therethrough.

In the present description, the thickness of the nonwoven fabric is measured as follows.

A sample is applied with pressure of constant pressure: 3 $g/cm^2$ by using FS-60DS (the area of the probe: 15 $cm^2$) manufactured by Daiei Kagaku Seiki MFG. Co., Ltd., and the thickness after 10 seconds after being applied with pressure is adopted as the thickness of the nonwoven fabric.

Further, the nonwoven fabric according to the present disclosure has a density preferably of 0.01 to 0.20 $g/m^3$, more preferably of 0.03 to 0.15 $g/m^3$, and even more preferably of 0.04 to 0.08 $g/m^3$. This is from the viewpoint of while maintaining the shape of the dented unit, letting the highly viscous excrement permeate therethrough.

In the present description, the density of the nonwoven fabric is calculated by dividing the basis weight of the nonwoven fabric by the thickness thereof.

The nonwoven fabric according to the present disclosure, in each of the plurality of dented units, preferably does not include a heat fused portion, for example, an embossed portion, at the bottom portion. This is because in the embossed portion, the fiber density is high, and it is difficult to let the highly viscous excrement permeate therethrough.

Further, although the nonwoven fabric according to the present disclosure may be a laminated body of the nonwoven fabric with two or more layers, the nonwoven fabric according to the present disclosure is preferably of a single layer. This is from the viewpoint of the permeation property of the highly viscous excrement.

The nonwoven fabric according to the present disclosure may be manufactured without being particularly limited, however, for example, may be manufactured by shaping (non-uniformly stretching) a commercially available nonwoven fabric.

Figure 13:
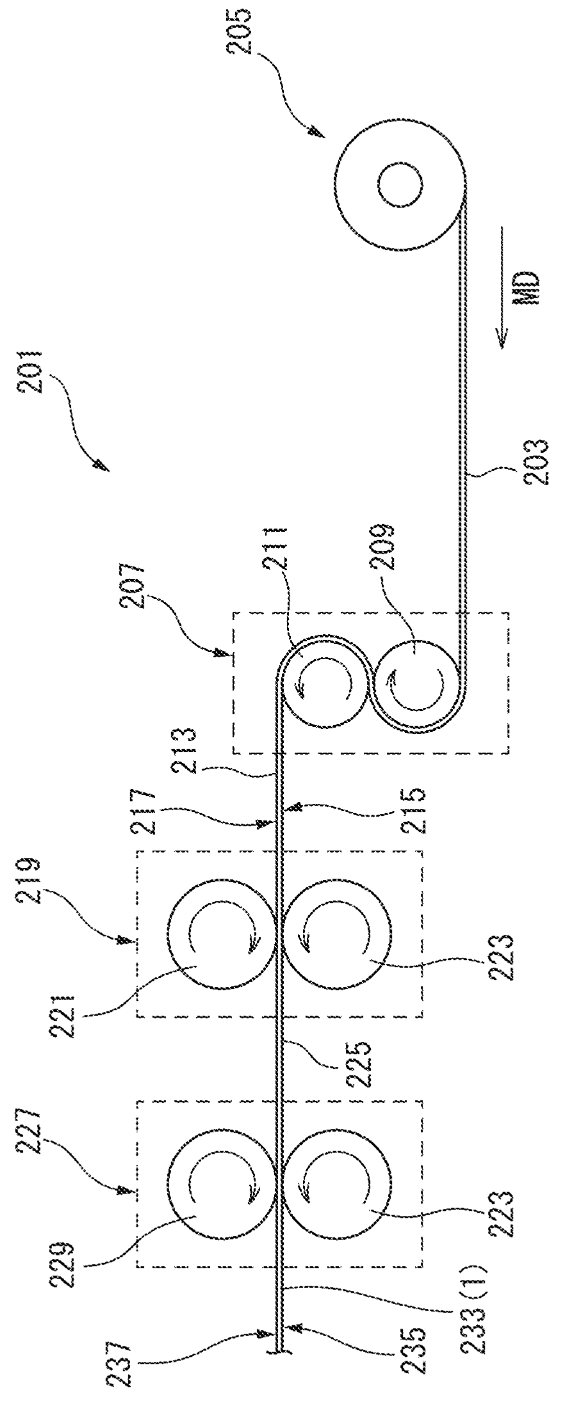
FIG. 13 is a view which schematically shows the manufacturing apparatus 201 that manufactures the nonwoven fabric of the present disclosure.
Figure 14:
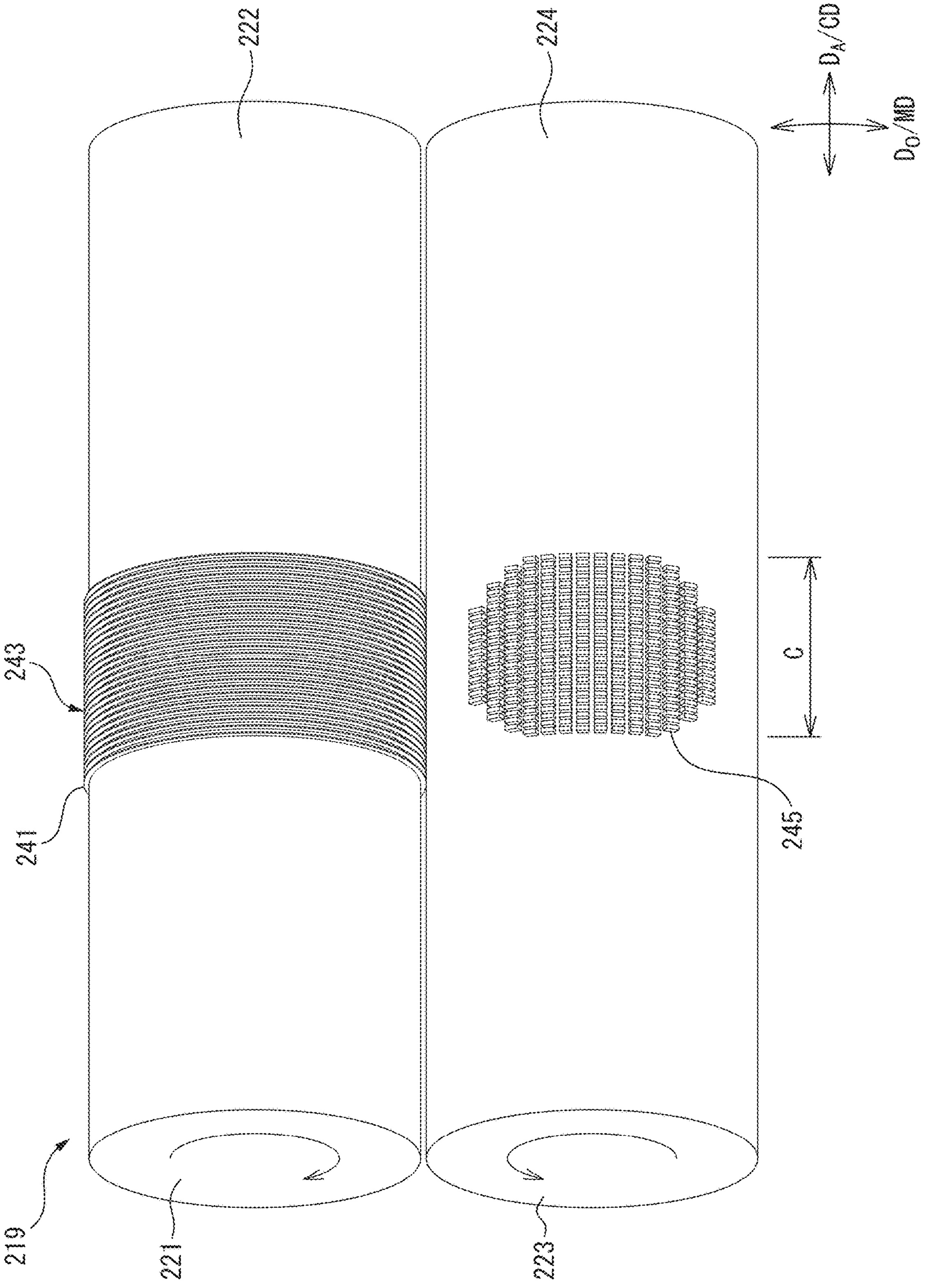
FIG. 14 is a perspective view which schematically shows the first shaping roll 221 and the second shaping roll 223 of the primary shaping device 219.
Figure 15:
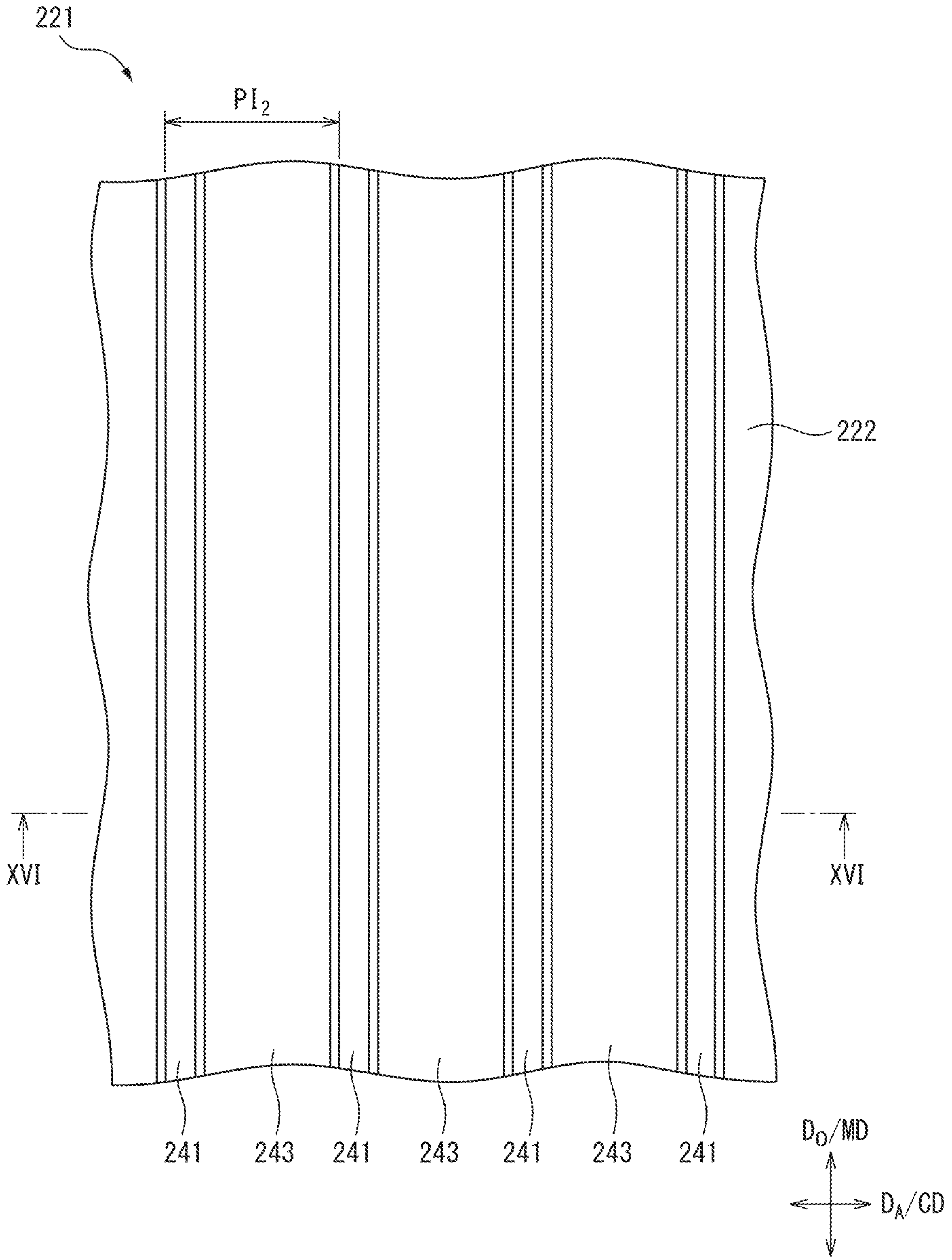
FIG. 15 is a main portion enlarged view which schematically shows the arrangement of the one direction protrusion 241 and the one direction groove 243 of the first shaping roll 221.

FIG. 13 to FIG. 25 are views so as to explain one example of the manufacturing method of the nonwoven fabric according to the present disclosure, and more specifically, one example of the manufacturing method of the nonwoven fabric 1 according to the first embodiment. To be specific, FIG. 13 is a view which schematically shows the manufacturing apparatus 201 that is used to manufacture the nonwoven fabric 1 according to the first embodiment. FIG. 14 is a perspective view which schematically shows the first shaping roll 221 and the second shaping roll 223 of the primary shaping device 219. FIG. 15 is a main portion enlarged view which schematically shows the arrangement of the one direction protrusion 241 and the one direction groove 243 of the first shaping roll 221.

Figure 16:
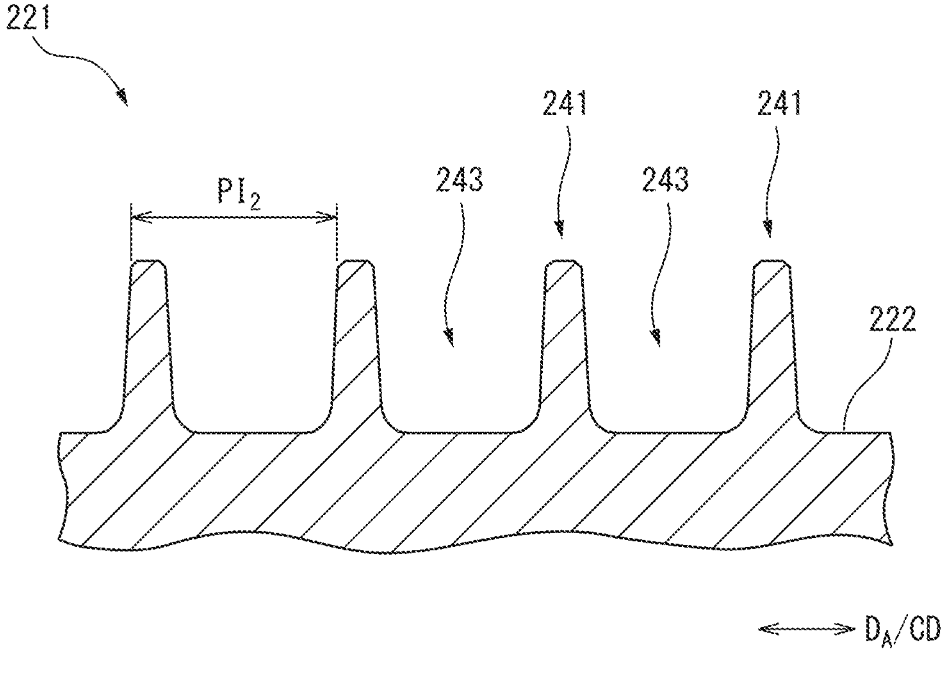
FIG. 16 is an end surface view at a XVI-XVI end surface of FIG. 15.
Figure 17:
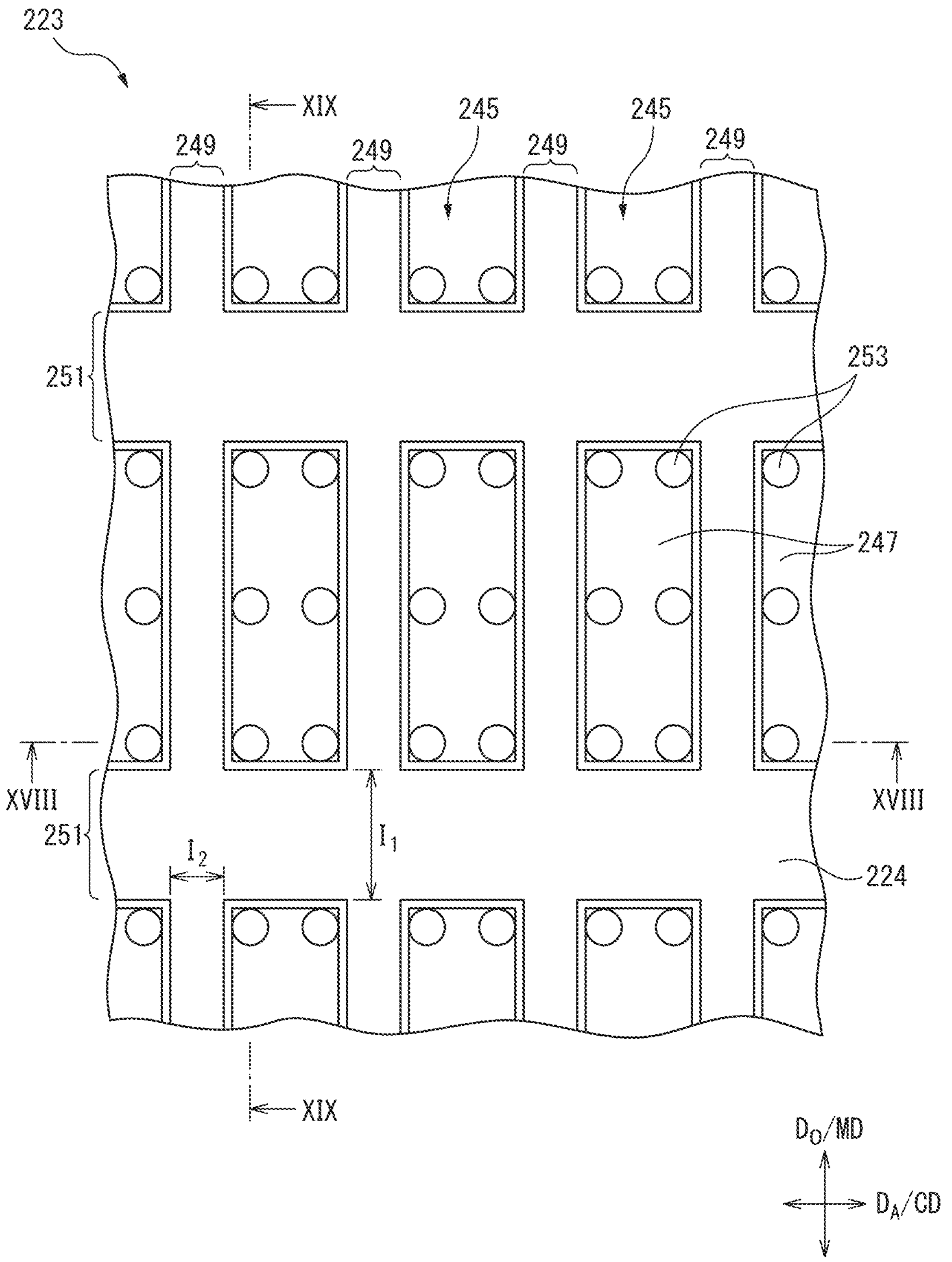
FIG. 17 is a main portion enlarged view which schematically shows the arrangement of the pin 245 of the second shaping roll 223.
Figure 18:
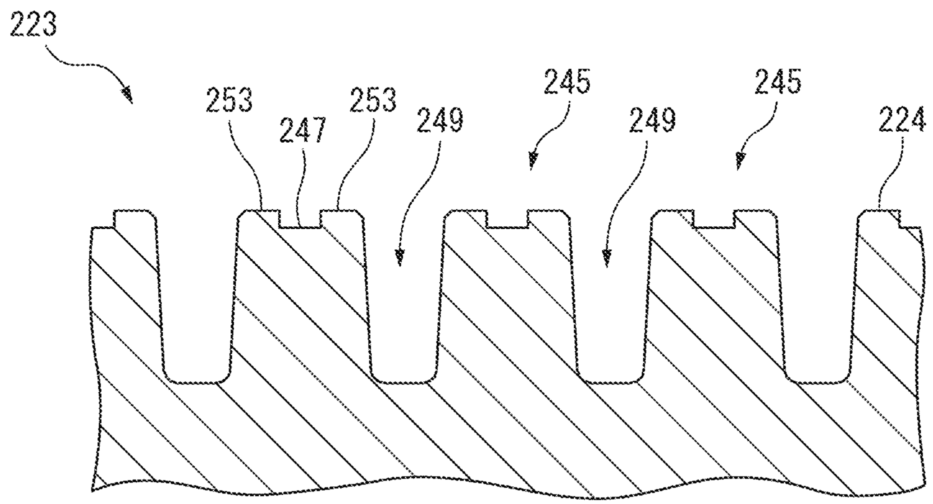
FIG. 18 is an end surface view at a XVIII-XVIII end surface of FIG. 17.
Figure 19:
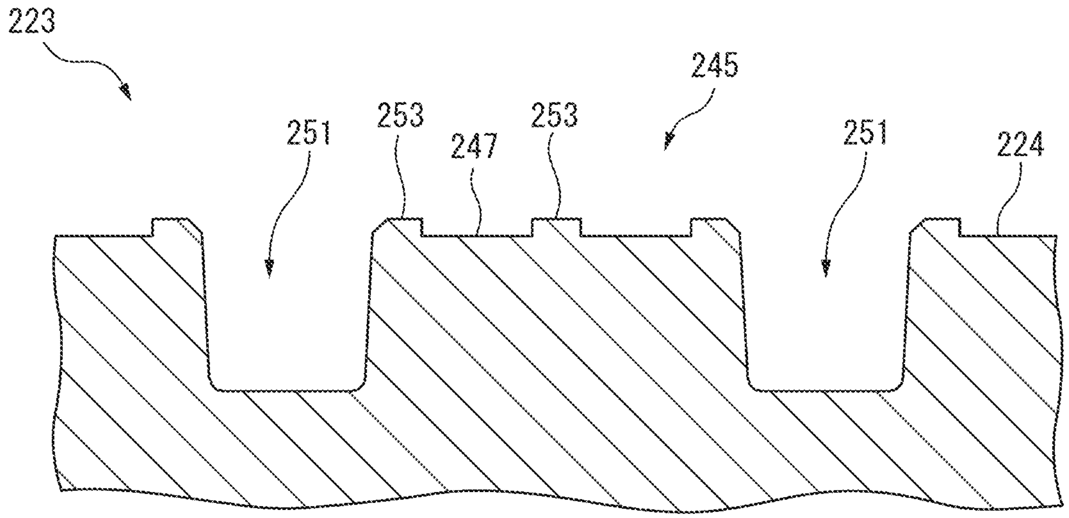
FIG. 19 is an end surface view at a XIX-XIX end surface of FIG. 17.
Figure 20:
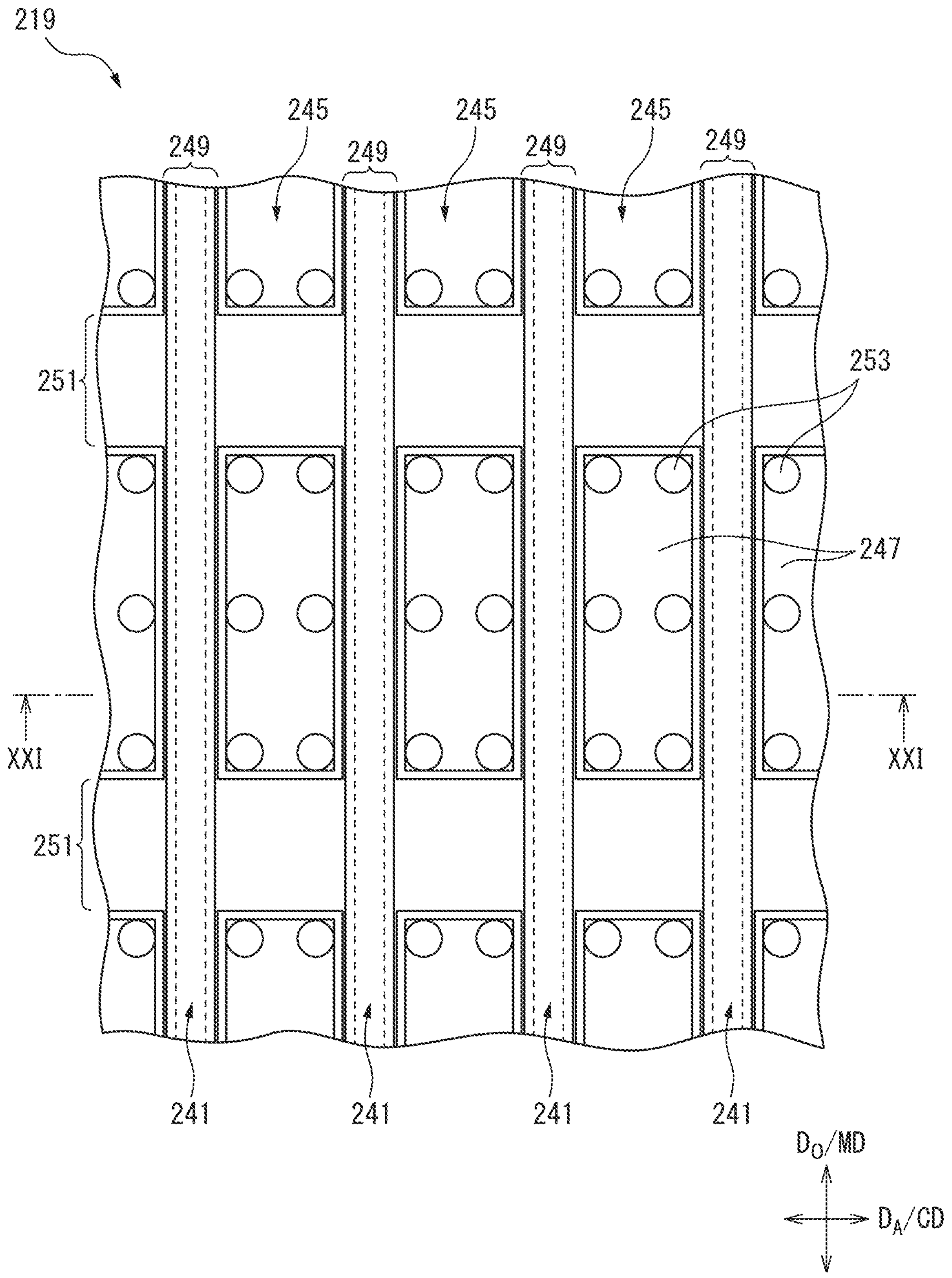
FIG. 20 is a view which shows the engagement of the first shaping roll 221 and the second shaping roll 223.
Figure 21:
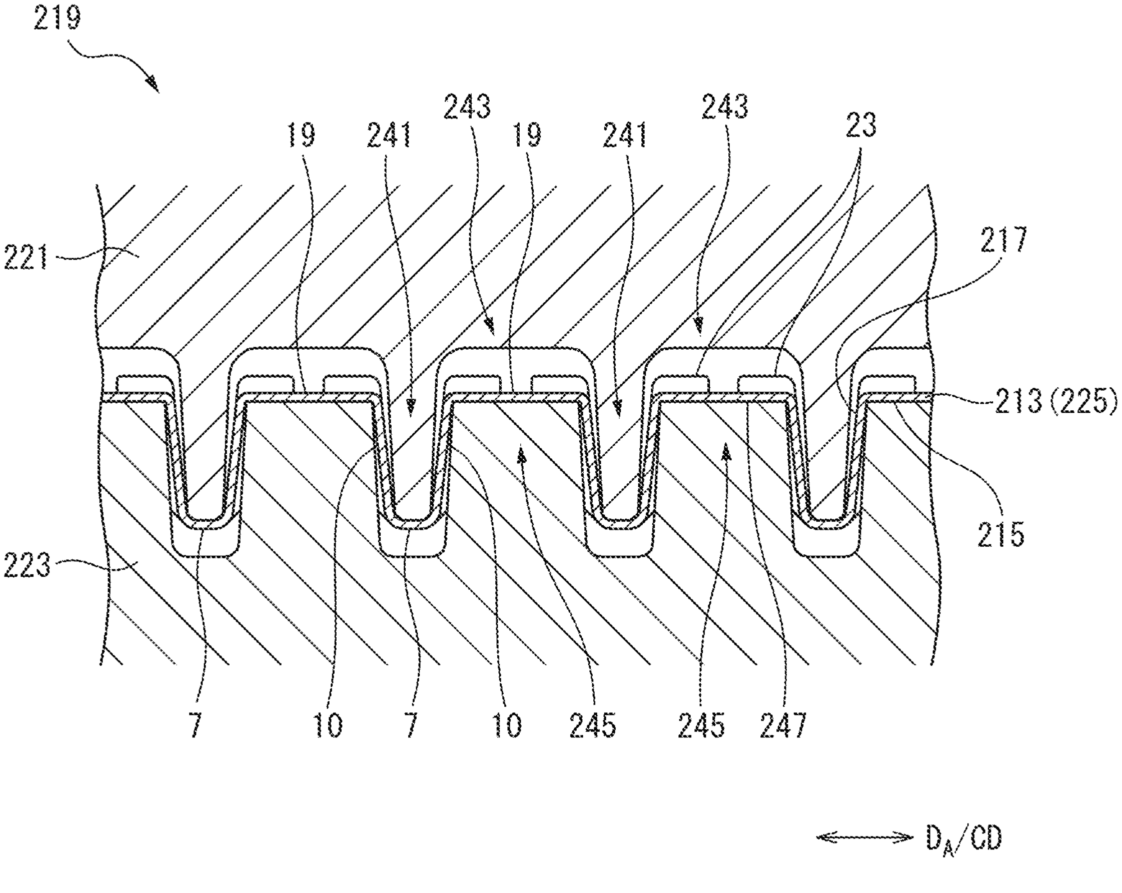
FIG. 21 is a sectional view which corresponds to the XXI-XXI sectional surface of FIG. 20, when the nonwoven fabric to be shaped 213 which has been preheated is subjected to primary shaping by the first shaping roll 221 and the second shaping roll 223.

FIG. 16 is an end surface view at a XVI-XVI end surface of FIG. 15. FIG. 17 is a main portion enlarged view which schematically shows the arrangement of the pin 245 of the second shaping roll 223. FIG. 18 and FIG. 19 are end surface views at a XVIII-XVIII end surface, and at a XIX-XIX end surface, respectively, of FIG. 17. FIG. 20 is a view which shows the engagement of the first shaping roll 221 and the second shaping roll 223. FIG. 21 is a sectional view which corresponds to the XXI-XXI sectional surface of FIG. 20, when the nonwoven fabric to be shaped 213 which has been preheated is subjected to primary shaping by the first shaping roll 221 and the second shaping roll 223.

Figure 22:
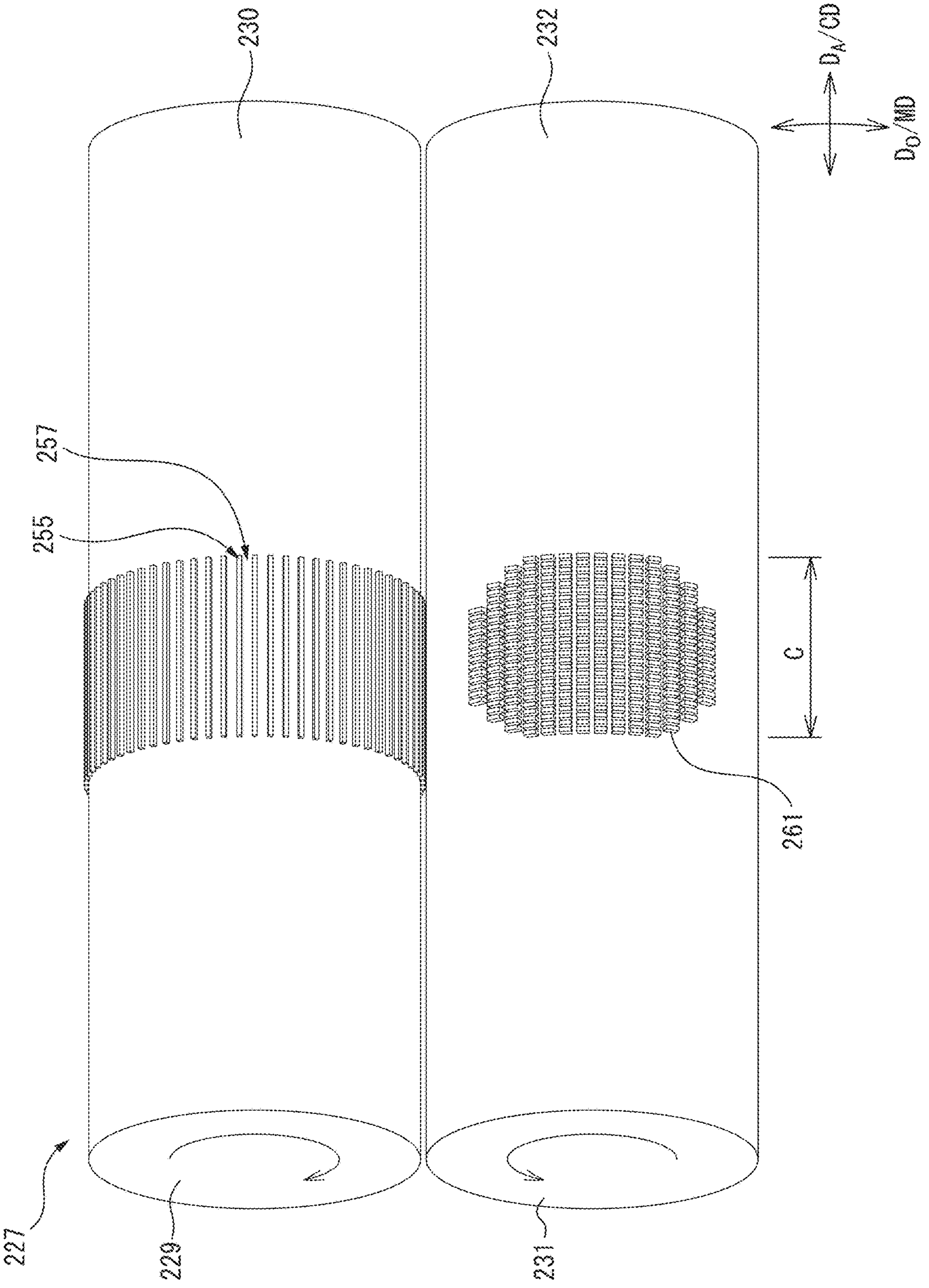
FIG. 22 is a perspective view which schematically shows the third shaping roll 229 and the fourth shaping roll 231 of the secondary shaping device 227.
Figure 23:
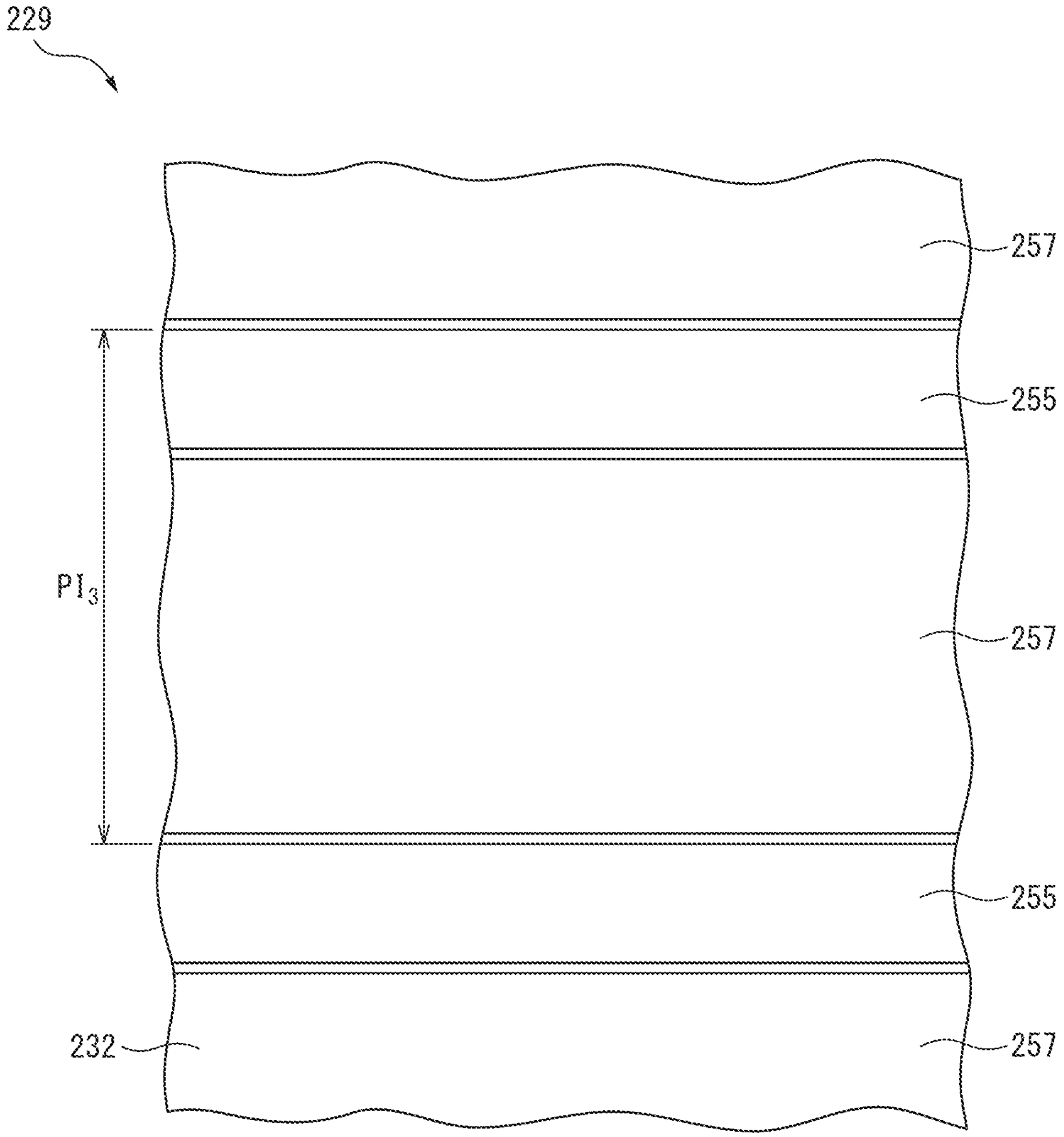
FIG. 23 is a main portion enlarged view which schematically shows the arrangement of the another direction protrusion 255 and the another direction groove 257 of the third shaping roll 229.
Figure 24:
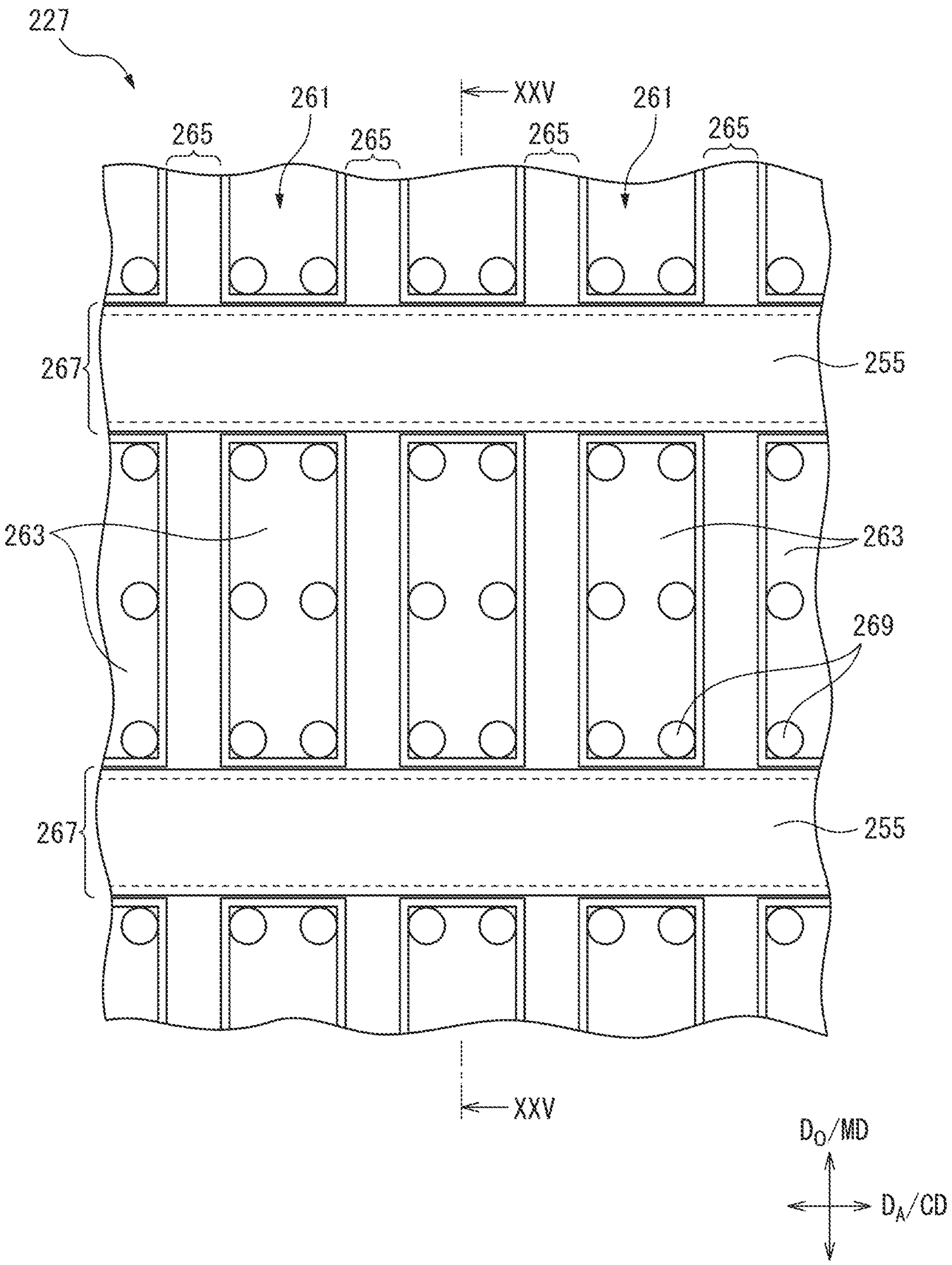
FIG. 24 is a view which shows the engagement of the third shaping roll 229 and the fourth shaping roll 231.
Figure 25:
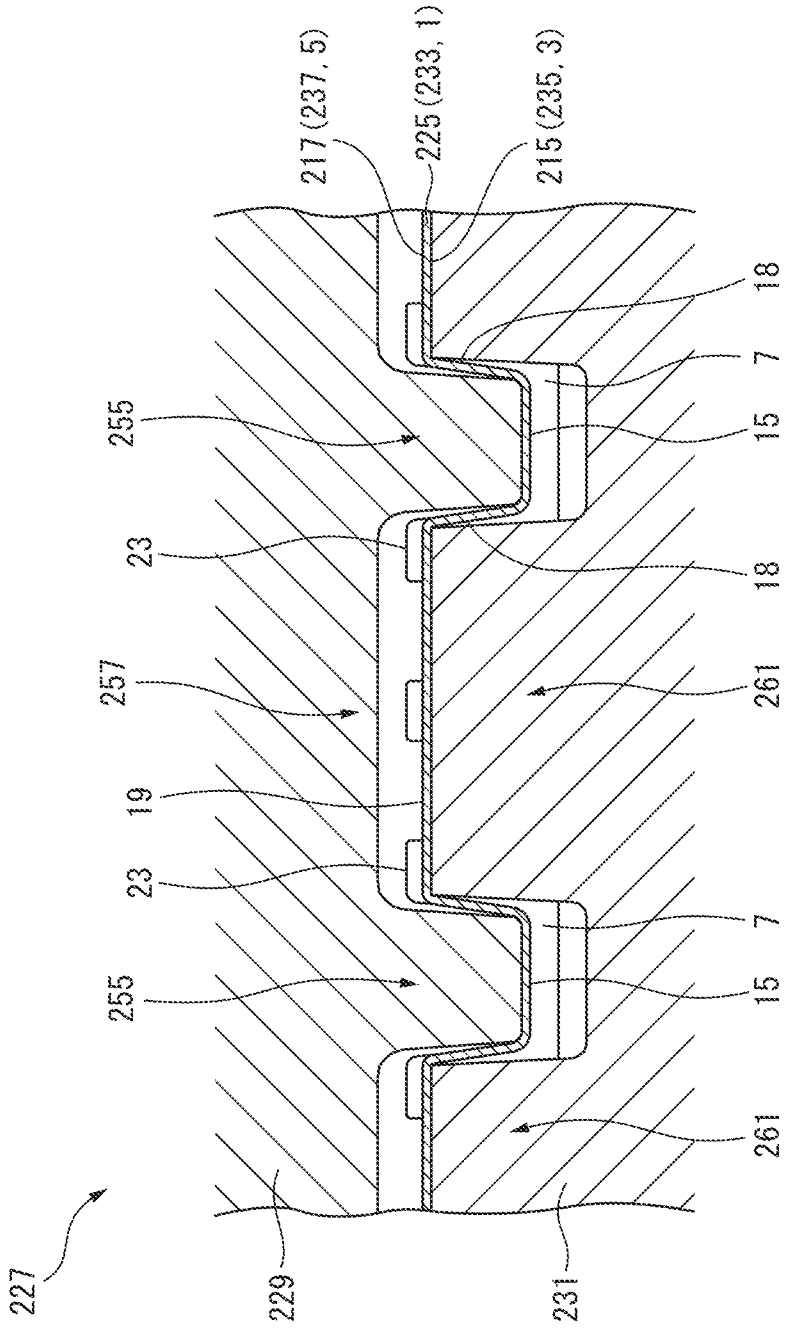
FIG. 25 is a sectional view which corresponds to the XXV-XXV sectional surface of FIG. 24, when the nonwoven fabric with primary shaping 225 is subjected to secondary shaping by the third shaping roll 229 and the fourth shaping roll 231.

FIG. 22 is a perspective view which schematically shows the third shaping roll 229 and the fourth shaping roll 231 of the secondary shaping device 227. FIG. 23 is a main portion enlarged view which schematically shows the arrangement of the another direction protrusion 255 and the another direction groove 257 of the third shaping roll 229. FIG. 24 is a view which shows the engagement of the third shaping roll 229 and the fourth shaping roll 231. FIG. 25 is a sectional view which corresponds to the XXV-XXV sectional surface of FIG. 24, when the nonwoven fabric with primary shaping 225 is subjected to secondary shaping by the third shaping roll 229 and the fourth shaping roll 231.

The manufacturing method, as shown in FIG. 13, is performed by [1] a preheating step, [2] a primary shaping step, and [3] a secondary shaping step.

The manufacturing apparatus 201 as shown in FIG. 13 includes, the unwinding device 205 in which the nonwoven fabric to be shaped 203 is wound in a rolled state and winds out the nonwoven fabric to be shaped 203 in the conveying direction MD; the preheating device 207 which preheats the nonwoven fabric to be shaped 203; the primary shaping device 219 which subjects the preheated nonwoven fabric to be shaped 213 to primary shaping so as to form the nonwoven fabric with primary shaping 225; and the secondary shaping device 227 which subjects the nonwoven fabric with primary shaping 225 to secondary shaping so as to form the nonwoven fabric with secondary shaping 233 (the nonwoven fabric 1).

[1] The Preheating Step

The preheating device 207 includes a pair of preheating rolls, that is, the first preheating roll 209 and the second preheating roll 211, and winds the nonwoven fabric to be shaped 203 to the rotating first preheating roll 209 so as to preheat the same, and thereafter, delivers the same to the rotating second preheating roll 211 so as to further preheat the same, and thus forms the preheated nonwoven fabric to be shaped 213.

The nonwoven fabric to be shaped preferably includes thermoplastic resin fibers. This is from the viewpoint of the shaping (non-uniformly stretching). Further, as the nonwoven fabric to be shaped, a nonwoven can be adopted without being particularly limited, as long as the nonwoven fabric is used in the technical field of absorbent articles, and for example, an air through nonwoven fabric, a spunbond nonwoven fabric, a point bond nonwoven fabric, a spunlace nonwoven fabric, a needle punch nonwoven fabric, a meltblown nonwoven fabric, and the combination of the above mentioned (for example, an SMS nonwoven fabric, etc.), etc., may be mentioned.

The preheating temperature is preferably close to the melting point of the thermoplastic resin fibers included in the nonwoven fabric to be shaped.

[2] The Primary Shaping Step

As shown in FIG. 14, the primary shaping device 219 includes a pair of shaping rolls, that is, the first shaping roll 221 on the upper side and the second shaping roll 223 on the lower side.

As shown in FIG. 14 to FIG. 16, the first shaping roll 221 includes, in the whole central region C in the perpendicular direction CD orthogonal to the conveying direction MD, the plurality of one direction protrusions 241 which extend in the one direction $D_O$ (the conveying direction MD), and the plurality of one direction grooves 243 which are disposed between the plurality of one direction protrusions 241 and extend in the one direction $D_O$ (the conveying direction MD). Incidentally, the plurality of one direction protrusions 241 and the plurality of one direction grooves 243 are alternately disposed in the another direction $D_A$ (the perpendicular direction CD) orthogonal to the one direction $D_O$ (the conveying direction MD).

Incidentally, the one direction $D_O$ and the another direction $D_A$ in connection with the primary shaping device 219 are respectively parallel to the conveying direction MD and the perpendicular direction CD.

To be specific, the plurality of one direction protrusions 241 are disposed in the central region C in the perpendicular direction CD of the outer circumferential surface 222 of the first shaping roll 221, with the pitch $PI_2$. The one direction protrusions 241 of the first shaping roll 221 are disposed so as to engage with the one direction groove portions 249 of the pins 245 of the second shaping roll 223 which are described later.

As shown in FIG. 14 and FIG. 17 to FIG. 19, the second shaping roll 223 includes, in a part of the central region C in the perpendicular direction CD orthogonal to the conveying direction MD, the plurality of pins 245 that include the tip portions 247. The plurality of pins 245 are disposed intermittently in the outer circumferential surface 224 of the second shaping roll 223, in the one direction $D_O$ (the conveying direction MD) with the interval $I_1$, and in the another direction $D_A$ (the perpendicular direction CD) with the interval $I_2$. In each of the tip portions 247 of the plurality of pins 245, six projections 253 are disposed.

In the second shaping roll 223, the plurality of pins 245 are disposed in the above described manner, whereby in between the plurality of pins 245, the plurality of one direction groove portions 249 which extend in the one direction $D_O$ and the plurality of another direction groove portions 251 which extend in the another direction $D_A$ are formed. The plurality of pins 245 of the second shaping roll 223 are disposed so as to engage with the one direction grooves 243 of the first shaping roll 221.

As shown in FIG. 20, in the primary shaping device 219, the first shaping roll 221 and the second shaping roll 223 are disposed so that the one direction protrusions 241 of the first shaping roll 221 engage with the one direction groove portions 249 of the second shaping roll 223, and the pins 245 of the second shaping roll 223 engage with the one direction grooves 243 of the first shaping roll 221.

As shown in FIG. 21, in the primary shaping step, the preheated nonwoven fabric to be shaped 213 is let to pass through between the first shaping roll 221 and the second shaping roll 223 which are rotating in a state of being engaged with each other, in the primary shaping device 219, and the preheated nonwoven fabric to be shaped 213 is stretched by being placed between the one direction protrusions 241 of the first shaping roll 221 on the upper side and the pins 245 of the second shaping roll 223 on the lower side which are engaged with each other, whereby the nonwoven fabric with primary shaping 225 is formed.

To be specific, the first shaping roll 221 on the upper side lets the one direction protrusions 241 be in contact with the second surface 217 of the preheated nonwoven fabric to be shaped 213, and pushes the contacting portion in the direction of the second shaping roll 223 on the lower side, whereby shapes the plurality of first ridge portions 7. Further, at this time, among the preheated nonwoven fabric to be shaped 213, the region in which the second ridge portions 15 are to be formed later is pushed downward, in conjunction with the pushing by the one direction protrusions 241 downward, and in the first surface, the semi-second ridge portions 259 in which the height is lower than desired, are formed.

The second shaping roll 223 on the lower side lets the plurality of pins 245 be in contact with the first surface 215 of the preheated nonwoven fabric to be shaped 213, and pushes the portion which is in contact with the tip portions 247 of the pins 245 to the inside of the one direction grooves 243 of the first shaping roll 221 on the upper side. As a result, among the preheated nonwoven fabric to be shaped 213, the portion which has been in contact with the tip portions 247 of the pins 245 is pushed strongly to the inside of the one direction grooves 243 so as to be shaped, and a part of the bottom portions 19 is formed. Further, the six projections 253 which are disposed in each of the tip portions 247 of the plurality of pins 245 form the recessed portions 23 in the bottom portions 19.

Incidentally, the first surface 215 and the second surface 217 of the preheated nonwoven fabric to be shaped 213 correspond respectively to the first surface 3 and the second surface 5 of the nonwoven fabric 1 according to the present disclosure.

The bottom portions 19 are formed, at the time of the primary shaping, in a state of the first shaping roll 221 on the upper side and the second shaping roll 223 on the lower side engaging the preheated nonwoven fabric to be shaped 213, by the tip portions 247 of the pins 245 pushing the contacting portion of the preheated nonwoven fabric to be shaped 213 to the inside of the one direction grooves 243. Accordingly, the bottom portions 19 tends to have a higher fiber density than the other portions, for example, the first top surface 9 and the first side surfaces 10 of the first ridge portions 7, and to have an excellent rigidity. Further, among the preheated nonwoven fabric to be shaped 213, the portion which is not in contact with the one direction protrusions 241 of the first shaping roll 221 and the with the pins 245 of the second shaping roll 223 is stretched at the time of the primary shaping, and tends to be lowered in the fiber density. Accordingly, the first side surfaces 10 of the first ridge portions 7 have a tendency of the fiber density being lower compared to the first top surface 9 and the bottom portions 19 of the first ridge portions 7.

Incidentally, at the time of performing the primary shaping step, in order to make it easier for the preheated nonwoven fabric to be shaped 213 to be non-uniformly stretched and to be shaped, the first shaping roll 221 and the second shaping roll 223 are preferably heated.

[3] The Secondary Shaping Step

As shown in FIG. 22, the secondary shaping device 227 includes a pair of shaping rolls, that is, the third shaping roll 229 on the upper side and the fourth shaping roll 231 on the lower side.

As shown in FIG. 22 and FIG. 23, the third shaping roll 229 includes, in the whole central region C in the perpendicular direction CD, the plurality of another direction protrusions 255 which extend in the another direction $D_A$ (the perpendicular direction CD), and the plurality of another direction grooves 257 which are disposed between the plurality of another direction protrusions 255 and extend in the another direction $D_A$ (the perpendicular direction CD). Incidentally, the plurality of another direction protrusions 255 and the plurality of another direction grooves 257 are alternately disposed in the one direction $D_O$ (the conveying direction MD).

To be specific, the plurality of another direction protrusions 255 are disposed in the central region C in the perpendicular direction CD of the outer circumferential surface 230 of the third shaping roll 229, with the pitch $PI_3$. The another direction protrusions 255 of the third shaping roll 229 are disposed so as to engage with the another direction groove portions 267 of the pins 261 of the fourth shaping roll 231 which are described later.

Incidentally, since the fourth shaping roll 231 has the same shape as the second shaping roll 223, the explanation of the fourth shaping roll 231 itself is omitted, however, the fourth shaping roll 231 includes, the pins 261, the tip portions 263, the one direction groove portions 265, and the another direction groove portions 267 which correspond to the pins 24, the tip portions 247, the one direction groove portions 249, and the another direction groove portions 251 of the second shaping roll 223, respectively.

As shown in FIG. 24, in the secondary shaping device 227, the third shaping roll 229 and the fourth shaping roll 231 are disposed so that the another direction protrusions 255 of the third shaping roll 229 engage with the another direction groove portions 267 of the fourth shaping roll 231, and the plurality of pins 261 of the fourth shaping roll 231 engage with the another direction grooves 257 of the third shaping roll 229.

As shown in FIG. 25, in the secondary shaping step, the nonwoven fabric with primary shaping 225 is let to pass through between the third shaping roll 229 and the fourth shaping roll 231 which are rotating in a state of being engaged with each other, in the secondary shaping device 227, and the nonwoven fabric with primary shaping 225 is stretched by being placed between the another direction protrusion 255 and the another direction groove 257 of the third shaping roll 229 on the upper side, and the pins 261 of the fourth shaping roll 231 on the lower side which are engaged with each other, whereby the nonwoven fabric with secondary shaping 233 (the nonwoven fabric 1) is formed.

To be specific, the third shaping roll 229 on the upper side lets the another direction protrusions 255 be in contact with the second surface 217 of the nonwoven fabric with primary shaping 225, and pushes the contacting portion in the direction of the fourth shaping roll 231 on the lower side, whereby shapes the plurality of second ridge portions 15.

The fourth shaping roll 231 on the lower side lets the plurality of pins 261 be in contact with the first surface 215 of the nonwoven fabric with primary shaping 225, and pushes the portion which is in contact with the tip portions 263 of the pins 261 to the inside of the another direction grooves 257 of the third shaping roll 229 on the upper side. As a result, among the nonwoven fabric with primary shaping 225, the portion which has been in contact with the tip portions 263 of the pins 261 is pushed strongly to the inside of the another direction grooves 257 so as to be shaped, whereby the bottom portions 19 are formed. Further, the six projections 269 which are disposed in each of the tip portions 263 of the plurality of pins 261 form the recessed portions 23 in the bottom portions 19.

Incidentally, the first surface 235 and the second surface 237 of the nonwoven fabric with secondary shaping 233 correspond respectively to the first surface 3 and the second surface 5 of the nonwoven fabric 1 according to the first embodiment.

The bottom portions 19 are formed, at the time of the secondary shaping, in a state of the third shaping roll 229 on the upper side and the fourth shaping roll 231 on the lower side engaging the nonwoven fabric with primary shaping 225, by the tip portions 263 of the pins 261 pushing the contacting portion of the nonwoven fabric with primary shaping 225 to the inside of the another direction groove 257. Accordingly, the bottom portions 19 tends to have a higher fiber density than the other portions, for example, the second top portion 16 of the second ridge portions 15, and to have an excellent rigidity. Further, among the nonwoven fabric with secondary shaping 233, the portion which is not in contact with the another direction protrusions 255 of the third shaping roll 229 and with the pins 261 of the fourth shaping roll 231 is stretched at the time of the secondary shaping, and tends to be lowered in the fiber density. Accordingly, the second side surfaces 18 of the second ridge portions 15 have a tendency of the fiber density being lower compared to the bottom portions 19.

The primary shaping device 219 and the secondary shaping device 227 are preferably operated in a synchronized manner. To be specific, the primary shaping device 219 and the secondary shaping device 227 are preferably operated in a synchronized manner so that the pins 245 of the second shaping roll 223 of the primary shaping device 219 and the pins 261 of the fourth shaping roll 231 of the secondary shaping device 227 come into contact with the same portion of the nonwoven fabric (the preheated nonwoven fabric to be shaped 213, and the nonwoven fabric with primary shaping 225). According to such a configuration, the bottom portions 19 and the second ridge portions 15 of the nonwoven fabric 1 are formed more clearly.

Incidentally, the primary shaping device 219 and the secondary shaping device 227 do not necessarily have to be operated in a synchronized manner. In such a case, there may be cases in which six or more recessed portions 23 are formed in each of the plurality of bottom portions 19 and the recessed portions 23 are formed in each of the plurality of second ridge portions 15, in the nonwoven fabric 1.

At the time of performing the secondary shaping step, in order to make it easier for the nonwoven fabric with primary shaping 225 to be non-uniformly stretched and to be shaped, the third shaping roll 229 and the fourth shaping roll 231 are preferably heated.

In the nonwoven fabric 1 according to the first embodiment, in a case the height of the second ridge portions 15 is not relatively high, in the above described manufacturing method, the secondary shaping step may be omitted. This is because, at the time of the primary shaping step, when pushing downward of the one direction protrusions 241, a configuration which corresponds to the second ridge portions although the height being low (which are the semi-second ridge portions) are formed.

The nonwoven fabric 1 according to the second embodiment may be manufactured in the same manner as the nonwoven fabric 1 according to the first embodiment, except for, for example, providing height differences alternately in the another direction $D_A$ for the height of the plurality of one direction protrusions 241, in the first shaping roll 221 of the primary shaping device 219.

The nonwoven fabric 1 according to the third embodiment may be manufactured in the same manner as the nonwoven fabric 1 according to the first embodiment, except for, for example, the following modifications:

(i) height differences are provided alternately in the another direction $D_A$ for the height of the plurality of one direction protrusions 241, in the first shaping roll 221 of the primary shaping device 219

Figure 26:
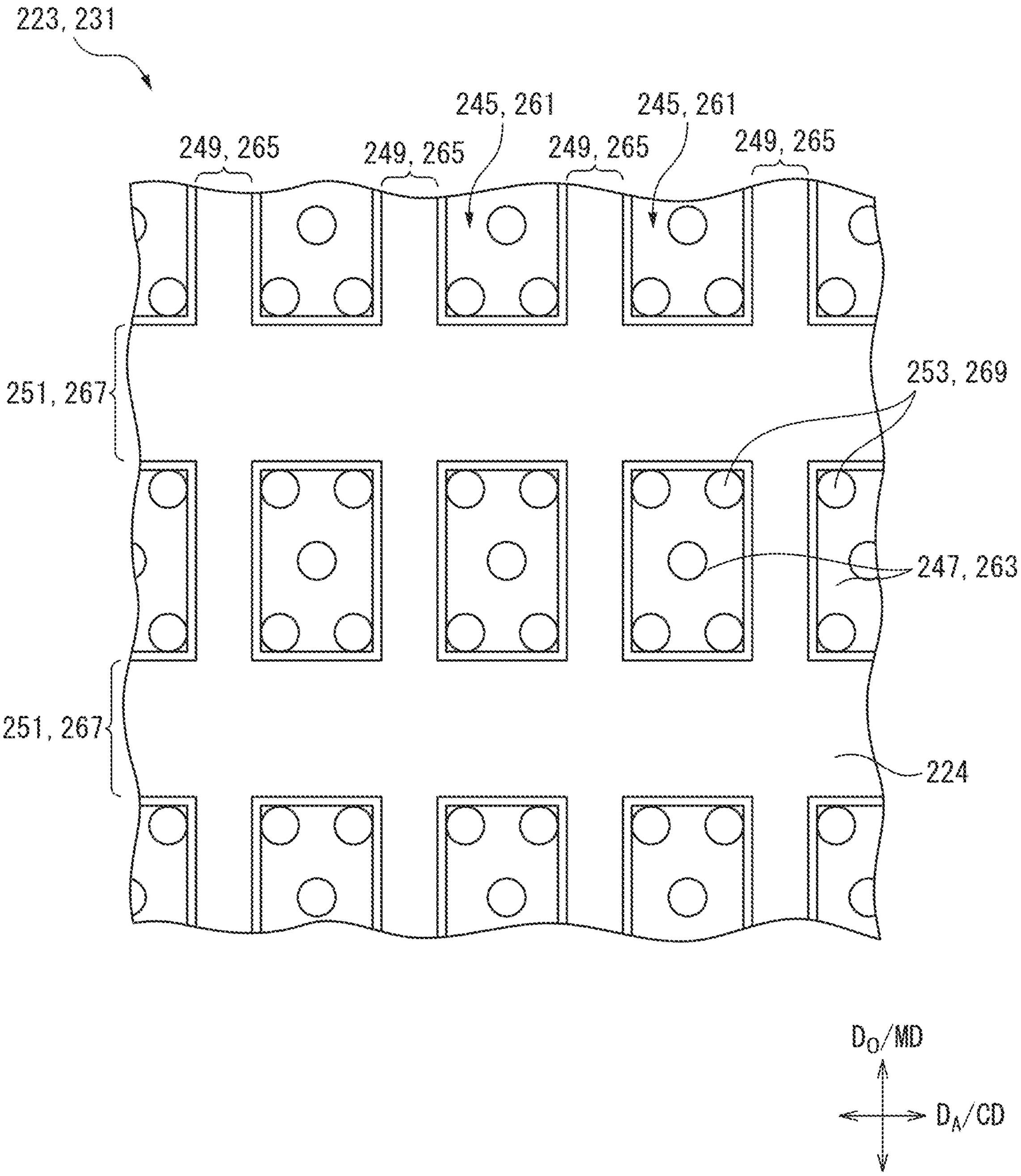
FIG. 26 is a view which schematically shows the second shaping roll 223 and the fourth shaping roll 231 so as to manufacture the nonwoven fabric 1 according to the third embodiment.

(ii) the second shaping roll 223 and the fourth shaping roll 231 are changed to the ones shown in FIG. 26

(iii) the another direction protrusions 255 of the third shaping roll 229 are changed so as to engage with the another direction groove portions 267 of the fourth shaping roll 231

Incidentally, the recessed portions 25 of the third ridge portions 41 are formed by the tip portions 247 which are disposed in the center of the pins 245 and by the tip portions 263 which are disposed in the center of the pins 261 shown in FIG. 26.

The nonwoven fabric 1 according to the fourth embodiment may be manufactured in the same manner as the nonwoven fabric 1 according to the first embodiment, except for, for example, the pins 245 of the second shaping roll 223 of the primary shaping device 219 and the pins 261 of the fourth shaping roll 231 of the secondary shaping device 227 not being provided with protrusions.

The nonwoven fabric according to the present disclosure can be used without being particularly limited, to whichever portion the nonwoven fabric is applicable in an absorbent article, and for example, the nonwoven fabric may be used as a liquid permeable sheet, a liquid impermeable sheet, an exterior sheet which is placed on the outer side of the liquid impermeable sheet, etc.

The nonwoven fabric for an absorbent article according to the present disclosure can be used so that the first surface and the second surface thereof configure the desired surfaces. For example, in a case in which the nonwoven fabric according to the present disclosure is used as a liquid permeable sheet of an absorbent article, the nonwoven fabric according to the present disclosure may be used so that the first surface or the second surface thereof configures the skin contact surface of the liquid permeable sheet. Further, in a case in which the nonwoven fabric according to the present disclosure is used as a liquid impermeable sheet of an absorbent article, the first surface or the second surface thereof may configure the outer surface of the liquid impermeable sheet.

The absorbent article to which the nonwoven fabric according to the present disclosure is applied is not particularly limited as long as the absorbent article absorbs highly viscous excrement, such as for example, highly viscous menstrual blood, vaginal discharge, loose stool, urine of the elderly, etc., and as such an absorbent article, for example, a disposable diaper, a sanitary napkin, a panty liner, an excretion pad, a pet sheet, etc., may be mentioned.

EXAMPLES

Hereinbelow, the present disclosure is explained by mentioning examples, however, the present disclosure is not limited to these examples.

Manufacturing Example 1

An air through nonwoven fabric is shaped and the nonwoven fabric according to the second embodiment (the nonwoven fabric No. 1) is manufactured. As the shaping step, the primary shaping step and the secondary shaping step are both performed. The characteristic values of the nonwoven fabric No. 1 are shown in Table 1.

Manufacturing Example 2

The nonwoven fabric No. 2 is manufactured according to Manufacturing Example 1, except for omitting the secondary shaping step. The characteristic values of the nonwoven fabric No. 2 are shown in Table 1.

Manufacturing Example 3

The nonwoven fabric No. 3 is manufactured from an air through nonwoven fabric according to the method described in Japanese Examined Patent Publication No. 5829326. The characteristic values of the nonwoven fabric No. 3 are shown in Table 1.

Manufacturing Example 4

The air through nonwoven fabric which is used in Manufacturing Example 1 is set as the nonwoven fabric No. 4.

Examples 1 and 2, and Comparative Examples 1 and 2

The nonwoven fabrics No. 1 to No. 4 are subjected to the loose stool adhesion test and the loose stool strike-through test. The results are shown in Table 1. The test methods are as follows.

[The Loose Stool Adhesion Test]

(1) An artificial loose stool which includes the following components with the following ratio is prepared.

ion exchanged water: 71.9 mass %

NaCl: 1.0 mass % glycerin: 15.0 mass %

NaCMC: 2.0 mass %

Triton X-100: 0.05 mass % red No. 102: 0.05 mass % powdered cellulose: 10.0 mass %

(2) The viscosity of the artificial loose stool is adjusted to 2000 mPa·s by ion exchanged water.

(3) A sample is cut into the size of 10×10 cm, and the initial mass of the sample: $m_1$ (g) is measured.

(4) 5 mL of the artificial loose stool is dropped to the range of approximately 3×3 cm of the sample in approximately 5 seconds, and the mass of the sample after the dropping: $m_2$ (g) is measured.

(5) On the sample including the artificial loose stool, a weight (the bottom surface size: 10×10 cm, mass: 2 kg, load: 20 gf/cm$^2$) in which an artificial leather (PBZ13001, manufactured by IDEATEX JAPAN Co., Ltd) is attached to the bottom surface thereof is placed.

(6) The weight is removed 1 minute after the weight is placed, and the mass of the sample after the test: $m_3$ (g) is measured.

(7) The loose stool adhesion rate (mass %) is calculated according to the following formula.

$$\text{The loose stool adhesion rate (mass \%)}=100\times(m_2-m_3)/(m_2-m_1)$$

[The Loose Stool Strike—Through Test]

(1) An upper side acrylic plate (50 cm×25 cm) which has an opening hole portion of a diameter of 30 mm, and in which a cylinder with an inner diameter 3 cm×a height 30 cm is attached above the opening hole portion, and a lower side acrylic plate (50 cm×25 cm) which has an opening hole portion of a diameter of 3 cm, and in which a cylinder with an inner diameter 30 mm×a height 15 cm is attached under the opening hole portion, are prepared.

(2) The sample is cut into 10×10 cm.

(3) The sample which is cut into 10×10 cm is disposed on the lower side acrylic plate, and the upper side acrylic plate is disposed thereon so that the positions of the opening hole portions match with each other. Further, a beaker placed on a scale is disposed under the cylinder of the lower side acrylic plate. Incidentally, the sample is disposed so that the first surface faces upward. Further, the nonwoven fabric No. 3 is also disposed so that the first surface faces upward.

(4) 150 g of the above described artificial loose stool is dropped on the cylinder of the upper side acrylic plate, and the amount of the loose stool (g) which has permeated the sample and has been accumulated in the beaker within 10 minutes after the dropping is measured, whereby the loose stool permeation amount is obtained.

TABLE 1

| | Example No. | | | |
|---|---|---|---|---|
| | Example 1 | Example 2 | Comparative Example 1 | Comparative Example 2 |
| Nonwoven fabric | | | | |
| No. | No. 1 | No. 2 | No. 3 | No. 4 |
| Basis weight (g/m$^2$) | 30 | 30 | 30 | 30 |
| Thickness (mm) | 2.0 | 2.0 | 1.0 | 0.7 |
| First ridge portions | | | | |
| Presence | Present | Present | Present | Not Present |
| Height (mm) | 1.6 | 1.6 | 1.0 | — |
| Width (mm) | 0.8 | 0.8 | 0.7 | — |
| Pitch (mm) | 3.0 | 3.0 | 1.5 | — |
| Second ridge portions | | | | |
| Presence | Present | Present | Not Present | Not Present |
| Height (mm) | 1.2 | 1.0 | — | — |
| Third ridge portions | | | | |
| Presence | Present | Present | Not Present | Not Present |
| Height (mm) | 0.5 | 0.4 | — | — |
| Pitch between first ridge portions (mm) | 1.5 | 1.5 | — | — |
| Test Results | | | | |
| Loose stool adhesion rate (mass %) | 11.9 | 9.2 | 19.5 | 37.0 |
| Loose stool permeation amount (g) | 40 | 30 | 20 | 0 |

The invention claimed is:

1. A nonwoven fabric for an absorbent article, said nonwoven fabric comprising:

a first surface and a second surface, and a first direction, a second direction that is orthogonal to the first direction, and a thickness direction, wherein the nonwoven fabric includes, in the first surface, a plurality of first ridge portions each extending in the first direction and including a first top surface that includes a first top portion, and a first side surface; and a plurality of first groove portions each extending in the first direction, the each of the plurality of first ridge portions and the each of the plurality of first groove portions being disposed alternately in the second direction, the nonwoven fabric includes, in the each of the plurality of first groove portions, in the first surface, a plurality of second ridge portions each being connected to two adjacent first ridge portions among the plurality of first ridge portions and including a second top portion; and a plurality of bottom portions, the each of the plurality of second ridge portions and the each of the plurality of bottom portions being disposed alternately in the first direction, the nonwoven fabric includes a plurality of dented units each including one of the plurality of bottom portions and being partitioned by virtual surfaces, each of the virtual surfaces extends in the thickness direction, passes through first top portions of two first ridge portions being adjacent to the one of the plurality of bottom portions, and passes through second top portions of two second ridge portions being adjacent to the one of the plurality of bottom portions, in the each of the plurality of dented units, a fiber density of the first side surface is lower than a fiber density of the first top surface, at least a part of the plurality of dented units includes, in the first surface of the bottom portion, a third ridge portion which extends in the first direction and is connected to the two second ridge portions, and a height of the first ridge portions is larger than a pitch between the third ridge portion and each of the first ridge portions.

2. The nonwoven fabric according to claim 1, wherein in the each of the plurality of dented units, heights of the two first ridge portions are higher than heights of the two second ridge portions.

3. The nonwoven fabric according to claim 1, wherein the each of the plurality of second ridge portions includes a second top surface including the second top portion, and a second side surface, and in the each of the plurality of dented units, a fiber density of the second side surface is lower than a fiber density of the second top surface.

4. The nonwoven fabric according to claim 1, wherein said at least the part of the plurality of dented units includes, in the first surface of the bottom portion, one or a plurality of recessed portions.

5. The nonwoven fabric according to claim 4, wherein the one or the plurality of recessed portions is disposed in a peripheral portion in the bottom portion, said peripheral portion being adjacent to at least one of the first ridge portions or the second ridge portions, and in said at least one of the first ridge portions or the second ridge portions, a fiber density of an adjacent portion which is adjacent to the one or the plurality of recessed portions is lower than a fiber density of a non-adjacent portion which is not adjacent to the one or the plurality of recessed portions.

6. The nonwoven fabric according to claim 4, wherein at least a part of the one or the plurality of recessed portions includes a penetration hole.

7. The nonwoven fabric according to claim 1, wherein the each of the plurality of second ridge portions is elongated in the second direction.

8. The nonwoven fabric according to claim 1, wherein the each of the plurality of dented units has a predetermined first direction length and a predetermined second direction length, and the plurality of dented units are disposed continuously in the first direction, with positions in the second direction being aligned.

9. The nonwoven fabric according to claim 1, wherein the nonwoven fabric includes, in the second surface, a plurality of first ridge portion corresponding groove portions each of which overlaps with a corresponding one of the plurality of first ridge portions in the thickness direction.

10. The nonwoven fabric according to claim 1, wherein the nonwoven fabric includes, in the second surface, a plurality of second ridge portion corresponding groove portions each of which overlaps with a corresponding one of the plurality of second ridge portions in the thickness direction.

11. The nonwoven fabric according to claim 4, wherein the at least the part of the plurality of dented units includes, in the second surface of the bottom portion, one or a plurality of protruded portions each of which overlaps with the one or the plurality of recessed portions in the thickness direction.

12. The nonwoven fabric according to claim 1, wherein the nonwoven fabric includes, in the second surface, a plurality of third ridge portion corresponding groove portions each of which overlaps with a corresponding one of a plurality of the third ridge portions in the thickness direction.

* * * * *